US012765884B2

(12) United States Patent
Greenhalgh

(10) Patent No.: US 12,765,884 B2
(45) Date of Patent: Oct. 20, 2026

(54) DECOMPRESSION SYSTEM AND METHODS OF USE

(71) Applicant: Travis Greenhalgh, Boca Raton, FL (US)

(72) Inventor: Travis Greenhalgh, Boca Raton, FL (US)

(73) Assignee: Travis Greenhalgh, Boca Raton, FL (US)

( * ) Notice: Subject to any disclaimer, the term of this patent is extended or adjusted under 35 U.S.C. 154(b) by 105 days.

(21) Appl. No.: 19/028,199

(22) Filed: Jan. 17, 2025

(65) Prior Publication Data

US 2025/0366868 A1 Dec. 4, 2025

Related U.S. Application Data

(62) Division of application No. 18/431,830, filed on Feb. 2, 2024, now Pat. No. 12,201,309.

(60) Provisional application No. 63/483,232, filed on Feb. 3, 2023.

(51) Int. Cl.

| | |
|---|---|
| ***A61B 17/16*** | (2006.01) |
| ***A61B 17/00*** | (2006.01) |
| ***A61B 17/3211*** | (2006.01) |
| ***A61B 17/56*** | (2006.01) |

(52) U.S. Cl.

CPC ...... *A61B 17/1671* (2013.01); *A61B 17/1613* (2013.01); *A61B 17/3211* (2013.01); *A61B 2017/00367* (2013.01); *A61B 2017/00982* (2013.01); *A61B 2017/564* (2013.01)

(58) Field of Classification Search

CPC ............ A61B 17/1671; A61B 17/1613; A61B 17/3211; A61B 2017/00367; A61B 2017/00982; A61B 2017/564

See application file for complete search history.

(56) References Cited

U.S. PATENT DOCUMENTS

| | | | |
|---|---|---|---|
| 7,799,033 | B2 | 9/2010 | Assell |
| 7,896,879 | B2 | 3/2011 | Solsberg |
| 8,048,080 | B2 | 11/2011 | Bleich |
| 8,221,424 | B2 | 7/2012 | Cha |
| 8,491,585 | B2 | 7/2013 | Hannani |
| 8,827,900 | B1 | 9/2014 | Pimenta |
| 8,870,890 | B2 | 10/2014 | Aschmann |

(Continued)

FOREIGN PATENT DOCUMENTS

| | | |
|---|---|---|
| WO | WO 2008/027923 | 3/2008 |
| WO | WO 2016/177271 A1 | 11/2016 |
| WO | WO 2022/207105 A1 | 10/2022 |

*Primary Examiner* — Kevin T Truong
*Assistant Examiner* — Diana Jones
(74) *Attorney, Agent, or Firm* — Knobbe, Martens, Olson & Bear, LLP

(57) ABSTRACT

A decompression surgery system includes an instrument shuttle configured to engage a first side of a target anatomical location, the instrument shuttle including a track. The system further includes a working channel configured to couple to and advance along the track of the instrument shuttle, the working channel having a distal end configured to engage a second side of the target anatomical location so that the target anatomical location is positioned between a portion of the instrument shuttle and the distal end of the working channel. The working channel is configured to receive one or more instruments therethrough.

20 Claims, 22 Drawing Sheets

(56) References Cited

U.S. PATENT DOCUMENTS 8,882,772 B2 11/2014 Solsberg
9,084,641 B2 7/2015 Chang
9,168,033 B2 10/2015 Hess
9,168,047 B2 10/2015 To
9,320,535 B2 4/2016 Zaretzka
9,414,884 B2 8/2016 Faehndrich
9,700,427 B2 7/2017 Assell
9,907,568 B2 3/2018 Ahmad
9,962,170 B2 5/2018 Jansen
10,143,486 B2 12/2018 Lauchner
10,568,641 B1 2/2020 Karasic
11,331,091 B2 5/2022 Jung
12,201,309 B2 1/2025 Greenhalgh
2002/0022704 A1 2/2002 Geibeler
2002/0022764 A1* 2/2002 Smith ................ A61B 17/3421
600/102
2005/0171549 A1 8/2005 Boehm
2006/0235452 A1 10/2006 Schomer
2007/0093841 A1 4/2007 Hoogland
2008/0033465 A1 2/2008 Schmitz
2008/0103504 A1 5/2008 Schmitz
2009/0018507 A1 1/2009 Schmitz
2009/0276048 A1 11/2009 Chirico
2011/0028978 A1 2/2011 Li
2012/0143206 A1 6/2012 Wallace
2012/0197320 A1 8/2012 Bereczki
2012/0221007 A1 8/2012 Batten
2013/0289399 A1* 10/2013 Choi .................. A61B 17/1608
606/86 R
2014/0114315 A1 4/2014 Leguidleguid
2014/0142379 A1 5/2014 Faehndrich
2014/0276848 A1 9/2014 Leguidleguid
2015/0265319 A1 9/2015 Ferree
2016/0095503 A1 4/2016 Davis
2017/0319244 A1 11/2017 Galino
2018/0028130 A1 2/2018 Choi
2018/0064471 A1 3/2018 Lee
2019/0125329 A1 5/2019 Simonson
2019/0216486 A1 7/2019 Weitzman
2019/0254768 A1 8/2019 Lieberman
2020/0229829 A1 7/2020 Ahrens
2020/0281621 A1 9/2020 Gill
2020/0330160 A1 10/2020 Dace
2021/0220146 A1 7/2021 Fabian
2021/0298843 A1 9/2021 Rezach
2021/0378689 A1 12/2021 Tyndall
2021/0386434 A1 12/2021 Tanaka
2021/0393408 A1 12/2021 Ginn
2022/0071663 A1 3/2022 Grob
2022/0071679 A9 3/2022 Naraghi
2022/0160375 A1 5/2022 Chin
2022/0211393 A1 7/2022 Messinger
2022/0265258 A1 8/2022 Choi
2022/0265285 A1 8/2022 Weitzman
2022/0304716 A1 9/2022 Cho
2022/0346822 A1* 11/2022 Tran ............... A61B 17/320016
2023/0104335 A1 4/2023 Choi
2024/0260975 A1 8/2024 Greenhalgh

* cited by examiner

DECOMPRESSION SYSTEM AND METHODS OF USE

INCORPORATION BY REFERENCE TO ANY PRIORITY APPLICATIONS

The present application is a divisional of U.S. application Ser. No. 18/431,830, entitled "DECOMPRESSION SYSTEM AND METHODS OF USE", filed Feb. 2, 2024, which claims priority benefit of Provisional Patent Application No. 63/483,232, entitled "DECOMPRESSION SYSTEM AND METHODS OF USE", filed Feb. 3, 2023, the entire disclosure of which is hereby expressly incorporated by reference. Any and all applications for which a foreign or domestic priority claim is identified in the Application Data Sheet as filed with the present application are hereby incorporated by reference under 37 CFR 1.57.

BACKGROUND

Field of the Invention

The present application relates to spinal surgery in general, and more particularly, to methods, systems, and apparatuses for decompression.

Description of the Related Art

Spinal stenosis is the narrowing of one or more spaces within the spine and can occur in the central canal surrounding the spinal cord or the lateral recess surrounding a peripheral nerve root. Reduction of space within the spine means a reduction in space available for the spinal cord and nerves that branch from the spinal cord. A tightened space can cause the spinal cord or nerves to become irritated, compressed, or pinched, which may result in back pain, weakness, and sciatica.

Spinal stenosis usually develops slowly over time, and it is most commonly caused by osteoarthritic changes that naturally occur in the spine as it ages. Depending on the location and severity of the stenosis, patients may feel pain, numbing, tingling, and/or weakness in the neck, back, arms, legs, hands, or feet.

More specifically, lumbar stenosis is the narrowing of the spinal canal or the tunnels through which nerves and other structures communicate with the lower back. Narrowing of the spinal canal usually occurs due to changes associated with aging that decrease the size of the spinal canal, including the movement of one of the vertebrae out of alignment.

Narrowing of the spinal canal or the side canals that protect the nerves often results in a pinching of the nerve root of the spinal cord. The nerves become increasingly irritated as the diameter of the canal becomes narrower. Spinal cord compression can lead to weakness or paralysis if left untreated.

Spinal stenosis can develop in anyone, but it is most common in men and women over the age of fifty. Younger individuals may be born with a congenital narrow spinal canal which can also result in spinal stenosis. Other conditions that affect the spine, such as cancer, scoliosis, or injury to the spine can put people at risk for developing spinal stenosis.

The spine consists of 24 vertebra plus the fused bones of the sacrum and coccyx, beginning at the base of the skull and ending at the pelvis. The spine supports an individual's body weight and protects the spinal cord and nerve roots. Each vertebrae consists of a body with a central opening (the spinal canal), flat areas (facet joints) where one vertebrae comes into contact with others above and below it, and bone protrusions along the sides of the vertebrae (transverse processes). Back portions, called the laminae, surround the cord and form a covering to the spinal canal. The part of the lamina where both sides come together creates a protrusion called the spinous process. Between each vertebrae body is a flat, round, soft cushion called an intervertebral disk that serves as a shock absorber. Ligaments are the strong fiber bands that hold the vertebrae together, keeping the spine stable and protecting the disks.

The spinal cord connects to the brain stem and sends and receives messages between the body and the brain. The spinal cord runs through the center of each vertebra of the spinal canal and is completely surrounded by the bony parts of the spine. Peripheral nerves roots are the initial segment of a bundle of nerve fibers that come off the spinal cord and exit the spinal column through side spaces between the vertebrae called the neural foramen. The nerve roots innervate and control all parts of the body.

Spinal stenosis has many causes. Degeneration of the structure of the spine can cause narrowing of the space around your spinal cord and nerves roots that exit through the neuro foramen. If the spinal cord and/or nerve roots become compressed or pinched, a variety of symptoms may appear including back pain, numbness, tingling, or weakness.

Osteoarthritis or bone growth/spurs is a condition that breaks down cartilage in the joints, including the spine. Cartilage is the protective covering of joints, and as it wears away, the bones begin to rub against each other like sandpaper. The body responds by growing new bone, but bone spurs or an overgrowth of the bone commonly occurs. Bone spurs on the vertebrae may extend into the spinal canal narrowing the openings and pinching nerves in the spine.

The narrowing of the spinal canal is usually a slow process and worsens over time. Although spinal stenosis can happen anywhere along the spinal column, the lower back and neck are common areas. When stenosis becomes worse there are many treatment options that can be sought, usually starting with the most conservative. Due to the complexity of spinal stenosis and the delicate nature of the spine, surgery is often considered when all other treatment options have failed or when symptoms become intolerable.

Surgery options include removing portions of bone, bony growths, facets, or disks that are crowding the spinal canal and pinching spinal nerves.

The most common type of surgery for spinal stenosis is laminectomy depression surgery which involves removing the lamina, the portion of the vertebra that covers and protects the spinal cord. Some ligaments and bone spurs may also be removed. The procedure creates room for the spinal cord and nerves, relieving the symptoms. Currently, this procedure requires a large incision and is performed open. This procedure also destabilizes the motion segment by removing the posterior tension band ligaments and structure which can later lead to instability and a need for spinal fusion.

Laminotomy is a partial laminectomy where only a small part of the lamina is removed in the area causing the most pressure on the nerve. This procedure can be performed open or minimally invasively.

Laminoplasty is a procedure performed in the neck (cervical) area only. Part of the lamina is removed to provide more canal space, then metal plates and screws are used to create a bridge across the area where bone was removed.

A foraminotomy is a procedure that opens the foramen, the area in the vertebrae where the nerve roots exit. Then, bone or tissue in this area is removed to provide more space for the nerve roots.

SUMMARY

Current surgical procedures have inherent risks, including nerve or spinal cord damage while performing the decompression. Instruments such as kerrisons, rongeurs, and pituitarys are used to extract bone and soft tissues to create more space for the neural elements. One such injury resulting from surgery is a dural tear which can cause pain and require arduous repair and results from tearing of the membrane that surrounds the spinal cord. Although the procedures have been performed for years, there continues to be injuries and risks. Systems, apparatuses, and methods for decompression are disclosed herein that can create an optimal surgical outcome in a minimally invasive fashion with decreased risk to the patient.

Also provided herein is a decompression surgery system. The system includes an instrument shuttle configured to engage a first side of a target anatomical location and a working channel configured to couple to and advance along the instrument shuttle to the target anatomical location. The working channel includes a distal end configured to engage a second side of the target anatomical location so that the target anatomical location is positioned between a portion of the instrument shuttle and the distal end of the working channel.

The instrument shuttle can include a guard having a guard plate configured to contact the first side of the target anatomical location. The guard plate can be pivotable about a pivot point of the instrument shuttle. The instrument shuttle can include a knob configured to rotate to change an angle of the guard plate. The guard can include a guard body and a pivot arm, wherein the knob is configured to rotate to cause axial movement of the pivot arm, wherein axial movement of the pivot arm is configured to cause the guard plate to pivot about the pivot point. The instrument shuttle can include a hook configured to engage the first side of the target anatomical location. The system can further include guard having a guard plate, wherein the guard plate is configured to contact the target anatomical location to secure the target anatomical location between the guard plate and the distal end of the working channel. The instrument shuttle can include a track, wherein the working channel is configured to couple to and advance along the track to the target anatomical location. The track can include a plurality of grooves, and the working channel can include a plurality of track arms having tips configured to releasably engage the plurality of grooves of the track. The system can include a multi-channel guide configured to be received within the working channel, the multi-channel guide having a plurality of channels configured to receive one or more instruments therethrough. The target anatomical location can be a lamina.

Also provided herein is a method of performing a decompression surgery. The method includes advancing an instrument shuttle to a target anatomical location through an incision, engaging a portion of the instrument shuttle with a first side of the target anatomical location, coupling a working channel to the instrument shuttle, and advancing the working channel to the target anatomical location along the instrument shuttle so that a distal end of the working channel engages a second side of the target anatomical location so that the target anatomical location is positioned between the portion of the instrument shuttle and the distal end of the working channel.

The method can include advancing an instrument through the working channel to the target anatomical location and cutting the target anatomical location using the instrument. The instrument can include a reamer, a trephine, a burr, or a drill. The method can include, prior to advancing the instrument through the working channel, inserting a multi-channel guide within the working channel, wherein advancing the instrument to the target anatomical location includes advancing the instrument through a channel of a plurality of channels of the multi-channel guide. The method can include, prior to advancing the instrument shuttle to the target anatomical location, making the incision with a scalpel, the scalpel including a blade coupled to a scalpel guide, wherein making the incision with the scalpel includes advancing the scalpel along a guide wire positioned within a slot of the scalpel guide. The instrument shuttle can include a hook configured to engage the first side of the target anatomical location. The method can include advancing a guard having a guard plate to the target anatomical location, and engaging the target anatomical location with the guard plate so that the target anatomical location is secure between the guard plate and the distal end of the working channel. The instrument shuttle can include a guard having a guard plate. Engaging the portion of the instrument shuttle with the first side of the target anatomical location can include engaging the guard plate with the first side of the target anatomical location. Advancing the working channel to the target anatomical location along the instrument shuttle so that the distal end of the working channel engages the second side of the target anatomical location can include securing the target anatomical location between the guard plate and the distal end of the working channel. The instrument shuttle can include a track. The method can include coupling the working channel to the track, wherein advancing the working channel to the target anatomical location along the instrument shuttle comprises advancing the instrument shuttle along the track.

DETAILED DESCRIPTION

Disclosed herein are instruments and methods for use in a decompression procedure. For example, in certain embodiments, the instruments and methods described herein can be used in a laminotomy. The instruments and methods described herein may be used to minimize risk during a decompression procedure (for example, when removing the lamina or portions thereof). For example, the instruments and methods described herein may prevent nerve or spinal cord damage during a surgical procedure.

In certain embodiments, a scalpel may be used in the systems and methods described herein. During a surgical procedure, the scalpel can be used to make an incision to cut through the skin, tissue, and muscle, for example, to access a target area. The incision can be used to create a tissue path to the target area. In some embodiments, the scalpel can be used in a laminectomy procedure. For example, the scalpel can be used to create an incision to a lamina. In some embodiments, a standard scalpel may be used. In other embodiments, the scalpel can be configured to be docked with a guide pin or guidewire. For example, in some embodiments, the scalpel can include or be coupled to a guide configured to couple with a guide pin or guidewire.

Figure 1A:
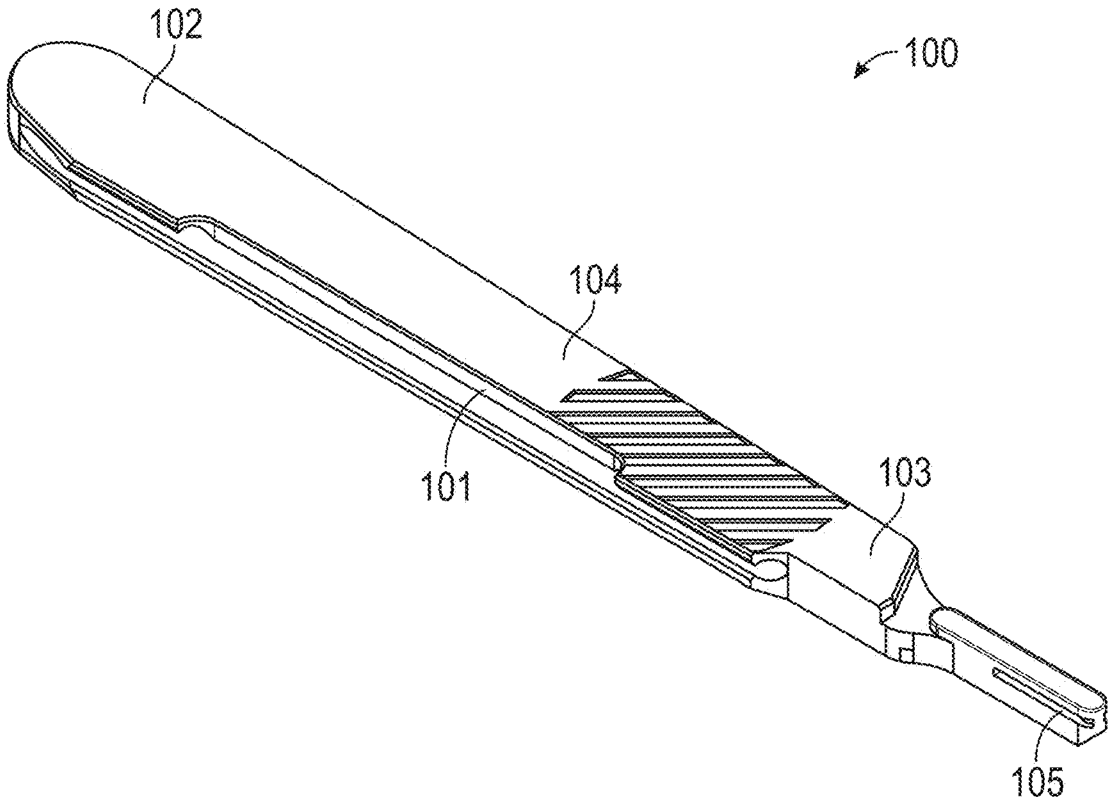
FIG. 1A depicts a perspective view of an embodiment of a scalpel guide.
Figure 1B:
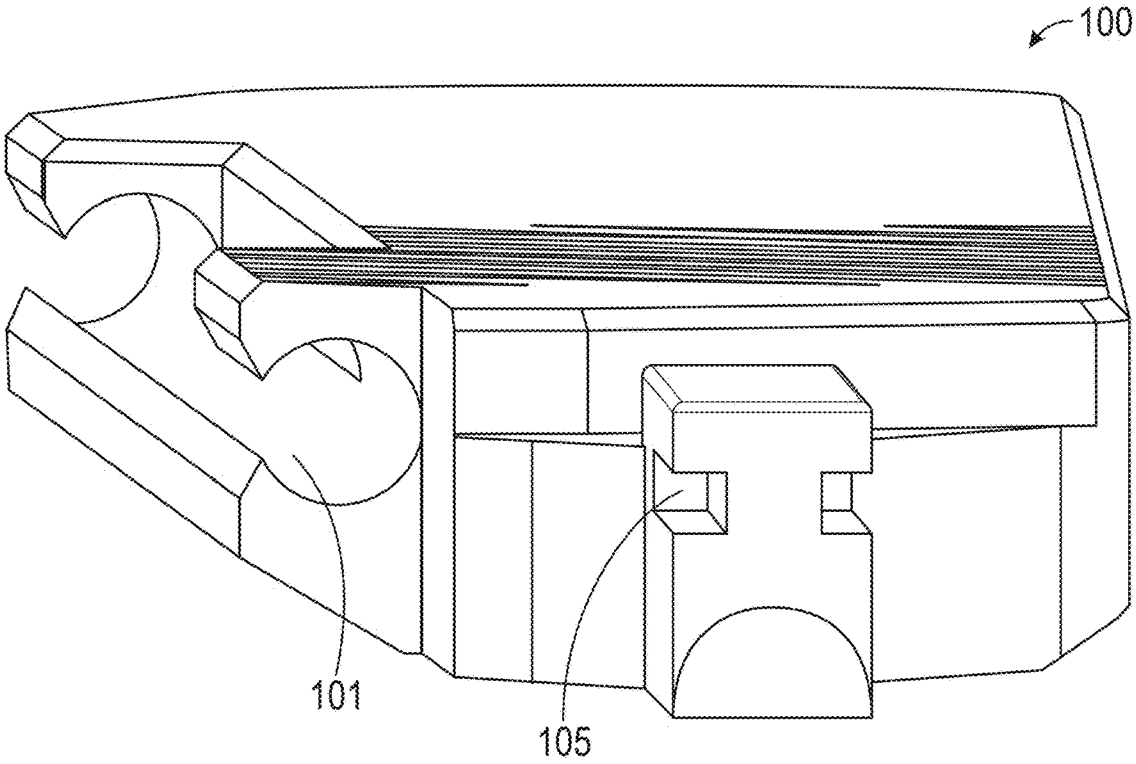
FIG. 1B depicts a front view of the scalpel guide of FIG. 1A.

FIG. 1A depicts a perspective view of a scalpel guide 100. FIG. 1B depicts a front view of the scalpel guide 100. In certain embodiments, the scalpel guide 100 may couple to a guide pin or guidewire. In certain embodiments, the scalpel guide 100 can include a channel or slot 101. The slot 101 can facilitate coupling of the guide 100 with other instruments. For example, in certain embodiments, the slot 101 can be configured to couple with a guide pin or guidewire. The scalpel guide 100 can include a handle 104. In certain embodiments, the slot 101 can extend between a proximal end 102 and a distal end 103 of the handle 104.

In certain embodiments, the scalpel guide 100 can include an attachment mechanism 105. In some embodiments, the attachment mechanism 105 can extend from the distal end 103 of the handle 104. The attachment mechanism 105 can be coupled to a blade or similar. In some embodiments, the attachment mechanism 105 can be configured to clip, strap, snap, receive, or otherwise engage a blade. For example, the attachment mechanism 105 can be a slot or recess configured to receive a blade. When a blade is coupled to the attachment mechanism 105, the guide 100 and blade can together form a scalpel.

In other embodiments, the attachment mechanism 105 can be configured to couple to (e.g., clip, strap, snap, receive or otherwise engage) a scalpel. In other embodiments, the blade can be provided with, integrally formed with, or irremovably connected to the guide 100, forming a scalpel.

Figure 2:
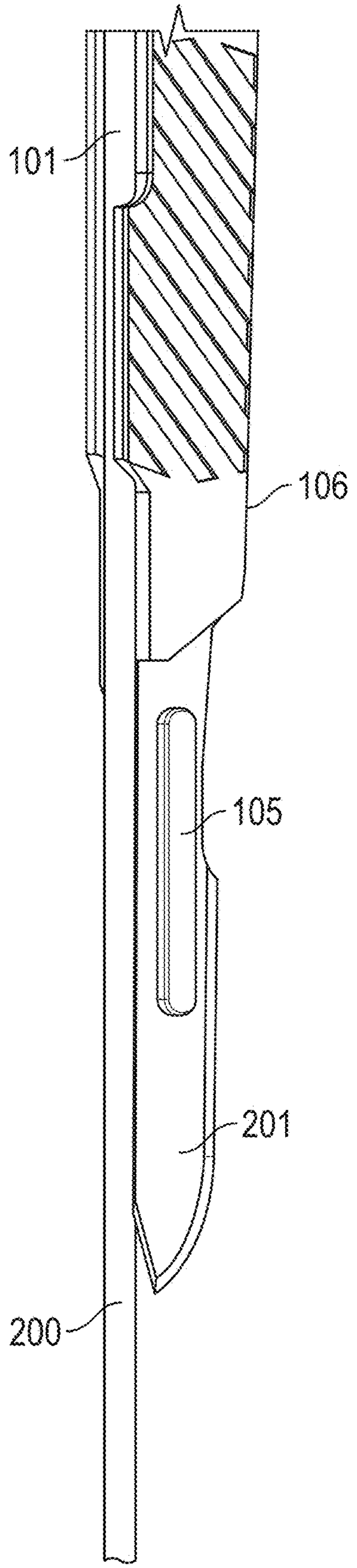
FIG. 2 depicts a side view of an embodiment of a scalpel including the scalpel guide of FIG. 1A and a blade.

As shown in FIG. 2, scalpel guide 100 and a blade 201 are coupled together to form a scalpel 106. The scalpel guide 100 can be coupled to a guidewire 200. For example, the slot 101 may be coupled to the guidewire 200. During a decompression procedure, the guide pin or guidewire 200 may be inserted into a target area, such as the lamina, spinous process, or other bony anatomy. The slot 101 can be slid down over the guidewire 200 to couple the scalpel 106 and the guidewire 200 together. In certain embodiments, the guidewire may be coupled to the scalpel 106 through clips, straps, or snaps instead of, or in addition to, the slot 101.

The scalpel 106 can be advanced along the guidewire 200 to a surgical site to create an incision to the area needing decompression. As shown in FIG. 2, the scalpel 106 may have a single blade 201. In other embodiments, the scalpel 106 may have two or more blades. For example, in some embodiments, the scalpel 106 can have two or more blades 201 coupled to the attachment mechanism 105. In other embodiments, the scalpel 106 can include a plurality of attachment mechanisms 105, each configured to couple to a unique blade 201. In some embodiments, two or more scalpels 106 can be coupled to the guidewire 200. In embodiments having two or more blades 201, the blades 201 can be spaced apart from one another to create a larger incision to the surgical location. For example, in some embodiments, two blades 201 can be positioned on opposite sides of the guidewire to create a larger incision. In some embodiments having a single blade 201, the user may advance the scalpel 106 to the target area along the guidewire 200 to create a first portion of an incision and then flip or rotate the scalpel 106 about the guidewire 200 (e.g., 180° about the guidewire) to position the blade 201 at a different position than used for the first portion of the incision. The scalpel 106 can then be advanced along the guidewire 200 to create a second portion of the incision, for example to create an incision large enough to pass dilators through the tissue and muscle to the surgical location.

Once the incision is made with scalpel 106, one or more dilators can be used to create a tissue path to the target area. For example, in certain embodiments, a first tissue dilator can be advanced over the guidewire 200 to the target area. In certain embodiments, a series of sequential dilators can follow until the site is dilated the appropriate amount for the procedure. In certain embodiments, one or more of the dilators may be used as a working channel for advancing additional instruments to the target area. In some embodiments, a separate working channel may be provided following dilation. In some embodiments, the working channels described herein can be guide tubes having lumens or channels for advancing additional instruments therethrough.

In certain embodiments of the systems and methods described herein, a positioning member or instrument shuttle may be provided. The instrument shuttle can be advanced within the incision towards the target area. Additional instruments (such as a dilator and/or working channel) may be coupled to the instrument shuttle and advanced along the instrument shuttle to the target area and/or retracted along the instrument shuttle from the target area. For example, in certain embodiments, the instrument shuttle can include a track, a rail, a gear drive, a ratchet mechanism, a linear actuator, or any other mechanism for translating an instrument along the instrument shuttle. Additional instruments (such as a dilator and/or working channel) may be coupled to the track or rail to advance the additional instruments to the target area. In some embodiments, the instrument shuttle can include engagement features, such as a hook or fastener, that can engage with and/or secure to the target area or anatomy adjacent the target area. Such engagement features may provide a stable and consistent path towards to the target area for instruments advancing along the instrument shuttle.

In certain embodiments of the systems and methods described herein, a guard may be provided. The guard may prevent damage to the surrounding anatomy (for example, the nerves and spinal cord) during a surgical procedure. The guard can protect the dura and the nerve roots when passing instruments, such as a trephine or Kerrison, to perform a decompression by removing part of the lamina, ligamentum flavum, etc., in a decompression procedure.

In certain embodiments, the guard may act as an instrument shuttle. In certain embodiments, the guard may include features, such as a track, a rail, a gear drive, a ratchet mechanism, a linear actuator, or any other suitable mechanism, for coupling to additional instruments and advancing the additional instruments to the target area. In other embodiments, a separate instrument shuttle may be provided. In certain embodiments, one or more features of the guard, such as a guard plate as described herein, can be an engagement feature or can include engagement features for engaging with or securing to the target anatomy to provide a stable and consistent path towards the target anatomy for instruments advancing along the guard.

Figure 3:
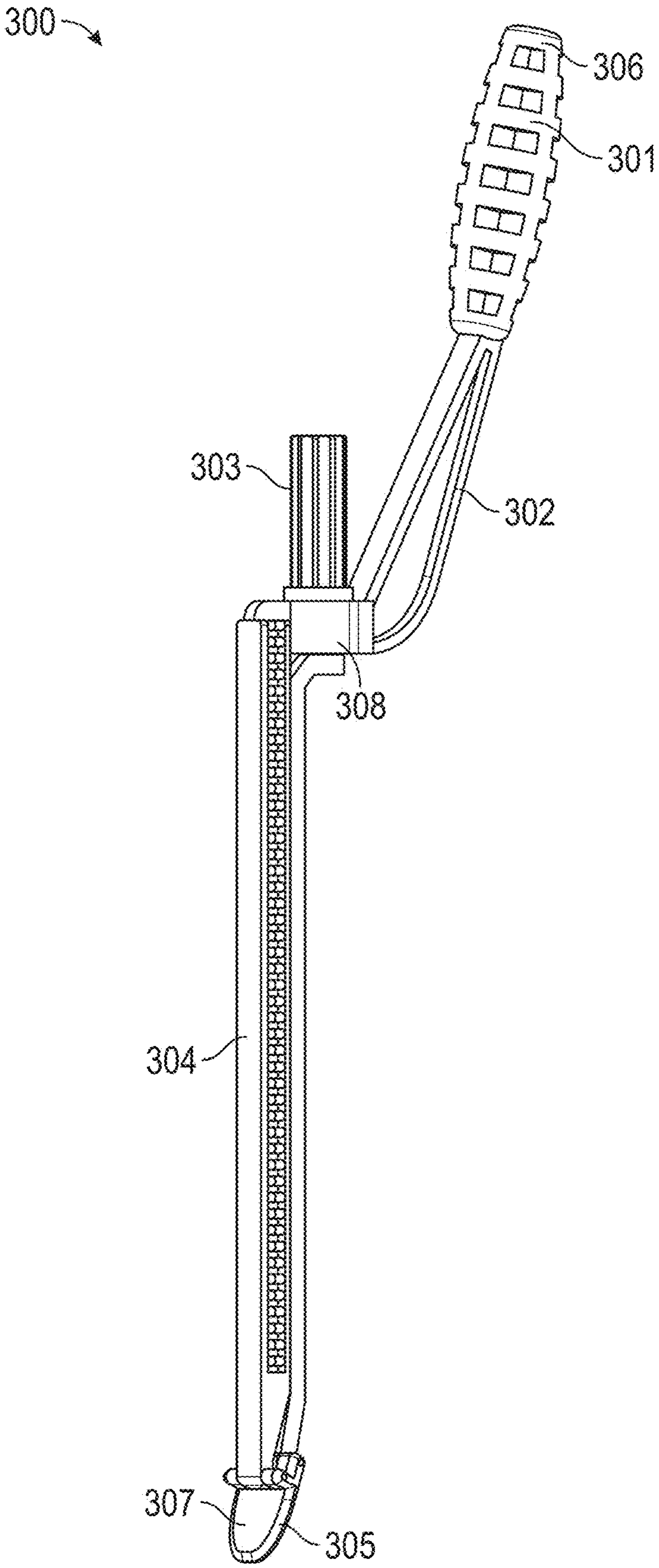
FIG. 3 depicts a perspective view of an embodiment of a guard.

Referring now to FIG. 3, a perspective view of a guard 300 is illustrated. In certain embodiments, the guard 300 can be used in a decompression procedure, such as a laminotomy. For example, in certain embodiments, after the muscle and tissue are dilated as described herein, the guard 300 may be passed through the tissue and muscle to a bony area covering the spinal canal or nerve root, such as the lamina. The guard 300 may have a proximal end 306. The proximal end 306 can include a handle 301 for manipulation by a user (e.g., a physician). The handle 301 of the guard 300 can be affixed to an arm 302. The arm 302 can be connected to a guard body 304.

In certain embodiments, the arm 302 can be pivotably coupled to the guard body 304 at a pivot point 308. that allows the arm 302 to pivot relative to the body 304. In certain embodiments, the arm 302 can be removably coupled to the guard body 304.

In certain embodiments, the guard 300 can include a guard plate 305. In certain embodiments, the guard plate 305 can be affixed at the distal end 307 of the guard 300. In certain embodiments, the guard plate 305 is pivotably coupled to the guard body 304 so that the guard plate 305 can be pivoted to different angles and/or positions.

In certain embodiments, the guard 300 can include a control mechanism for controlling the angle and/or position of the guard plate 305. For example, as shown in FIG. 3, the guard 300 can include a knob 303 that can be manipulated to control the angle and/or position of the guard plate 305. The knob 303 can be positioned between the guard arm 302 and the body 304 proximate to the guard handle 301. A guard plate pivot point 401 may connect the guard plate 305 to the guard body 304. In some embodiments there are two or more pivot points 401 connecting the guard plate to the guard body 304.

In certain embodiments, the guard plate 305 and the knob 303 are connected by a pivoting arm (see FIG. 6A) so that when the knob 303 is turned, the guard plate 305 pivots in response. The pivot point 401 may connect the pivoting arm to the guard plate 305. As the pivoting arm moves up and down, the guard plate 305 moves about the pivot point 401. Several angles of the guard plate 305 may be possible through adjustment of the knob and pivoting arm.

In some embodiments, during a decompression procedure, the guard 300 is advanced through the tissue path and placed proximate to the target anatomy (e.g., the lamina, spinous process, or facet) once it is exposed. The guard plate 305 can be adjusted to fit under the target anatomy. For example, the guard 300 may be manipulated by the handle 301 or the body 304 to rotate and/or translate the guard 300. For example, the handle 301 may be manipulated to maneuver the guard 300 through muscle and other tissue.

In certain embodiments, the guard plate 305 can be rotated (e.g., about the pivot point 401), articulated, and/or otherwise maneuvered to pivot up or down to pass under the lamina or other target anatomy, for example, by manipulation of the knob 303. In certain embodiments, the guard plate 305 can be positioned to contact a side (e.g., underside) of the target anatomy to create a safety stop for instruments driven through the opposite side (e.g., top side) of the target anatomy to prevent damage to surrounding tissue, organs, bones, or other body parts (e.g., dura, nerve roots, etc.). The guard plate 305 can be positioned around the target anatomy to accommodate various angles for the protection of surrounding internal anatomy. Once the guard plate 305 is in the desired position. The orientation of the guard plate 305 can be fixed or locked.

In certain embodiments, the distal end 307 of the guard 300 (e.g., a distal end of the guard plate 305) may be bulleted or tapered to pass through or dissect muscle or other tissue. In certain embodiments, the guard plate 305 can be flat, convex, concave, and/or come in a variety of shapes to accommodate different anatomies or regions of the spine. In certain embodiments, a plurality of guards 300 having different shapes, dimensions, and/or other features may be provided for different anatomies or regions of the spine. In some embodiments, a plurality of guards 300 having guard bodies 304 of different lengths may be provided to treat different patients or reach different areas within the body.

Figure 4A:
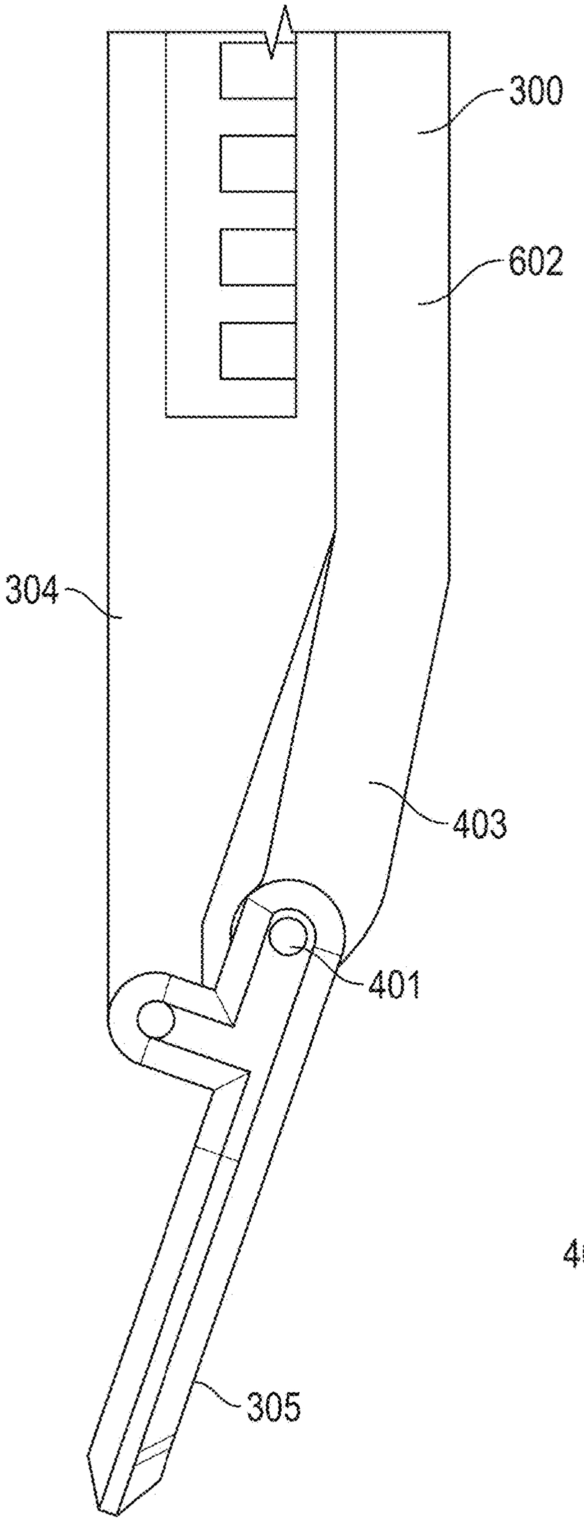
FIG. 4A depicts an enlarged side view of a distal end of the guard of FIG. 3.

In certain embodiments, as illustrated in FIG. 4A, the guard plate 305 may be in a first extended or straightened position upon insertion into the body. The first position of the guard plate 305 in relation to the guard body 304 allows the physician to advance the guard 300 parallel to or generally parallel to the lamina or target anatomy, which may be a precise and tight space.

In alternative embodiments, the guard plate 305 may not pivot relative to the guard body 304, but instead, the guard plate 305 may be fixed at a specific angle. In certain embodiments, the guard plate 305 is fixed at specific angles may be integrally formed with the guard body 304. In certain embodiments, a plurality of guards 300 with fixed guard plates 305 having different predetermined angles may be provided. Fixed guard plates 305 having different predetermined angles may be used for different anatomies. In certain embodiments, a fixed guard plate 305 may have a reduced risk of breaking or damaging in comparison to a pivoting guard plate 305. The fixed angles include one or more of 15 degrees, 30 degrees, 45 degrees, 60 degrees, 75 degrees, 90 degrees, less than 15 degrees, between 0 degrees and 30 degrees, between 15 degrees and 30 degrees, between 30 degrees and 45 degrees, between 45 degrees and 60 degrees, between 60 degrees and 75 degrees, between 75 degrees and 90 degrees, between 15 degrees and 90 degrees, between 30 degrees and 60 degrees, between 60 degrees and 90 degrees, between 45 degrees and 90 degrees, or any other suitable angle.

In some embodiments, the guard body 304 may have a distal area 403 that is designed to be textured, knurled, have teeth, or have other features to help grip the bone and prevent slipping upon insertion. Alternatively, the distal area 403 may be feature-free to allow for smoother insertion and removal of the guard.

Figure 4B:
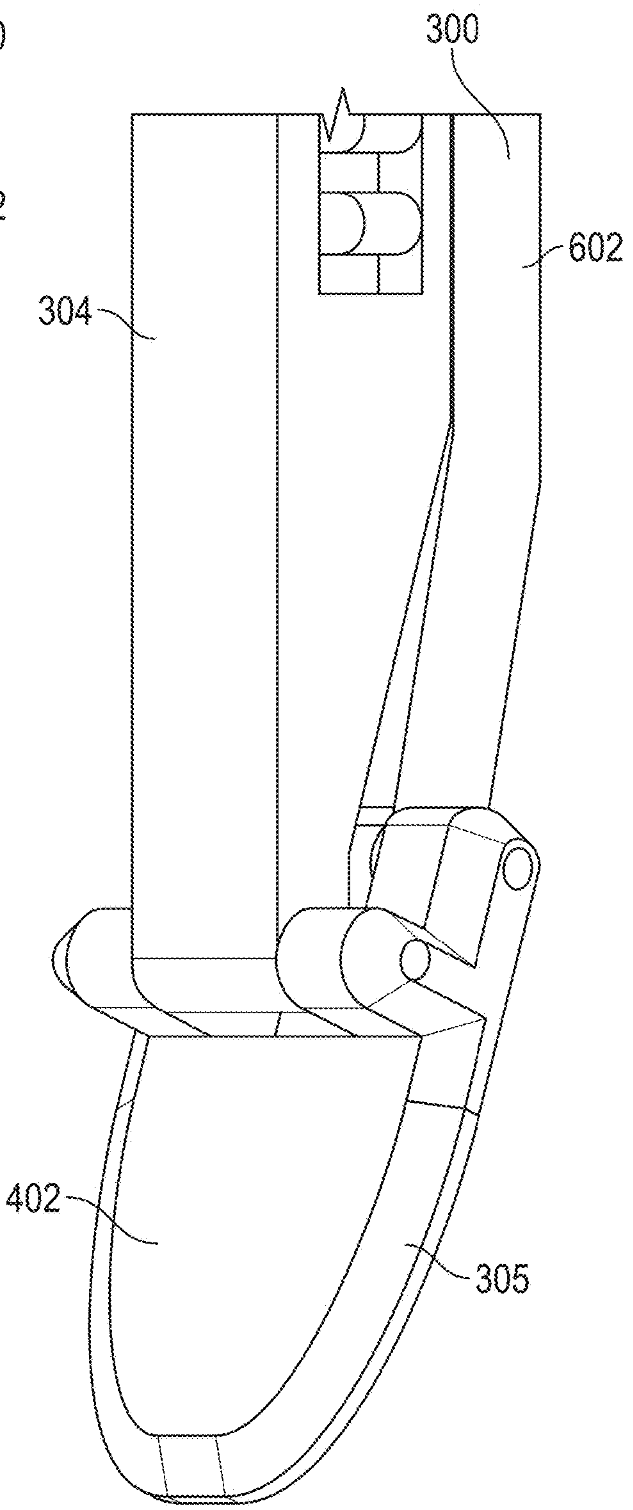
FIG. 4B depicts an enlarged perspective view of the distal end of the guard of FIG. 3.

As illustrated in FIG. 4B, the guard plate 305 can include a top surface 402. The top surface 402 can be positioned to contact the bottom of the lamina or target anatomy when the guard plate 305 is pivoted from the first position to a second position. Once the guard plate 305 is pivoted under the target area (e.g., the lamina), the guard plate 305 can be fixed into position and serve as a stopping point during later steps of the surgical procedure (e.g., laminotomy).

In certain embodiments, the guard plate 305 may take on other shapes and configurations. In certain embodiments, the guard plate 305 may contain features for gripping to the bone. Alternatively, the guard plate may be specifically dimensioned for the size and shape of the anatomy being targeted.

Figure 5B:
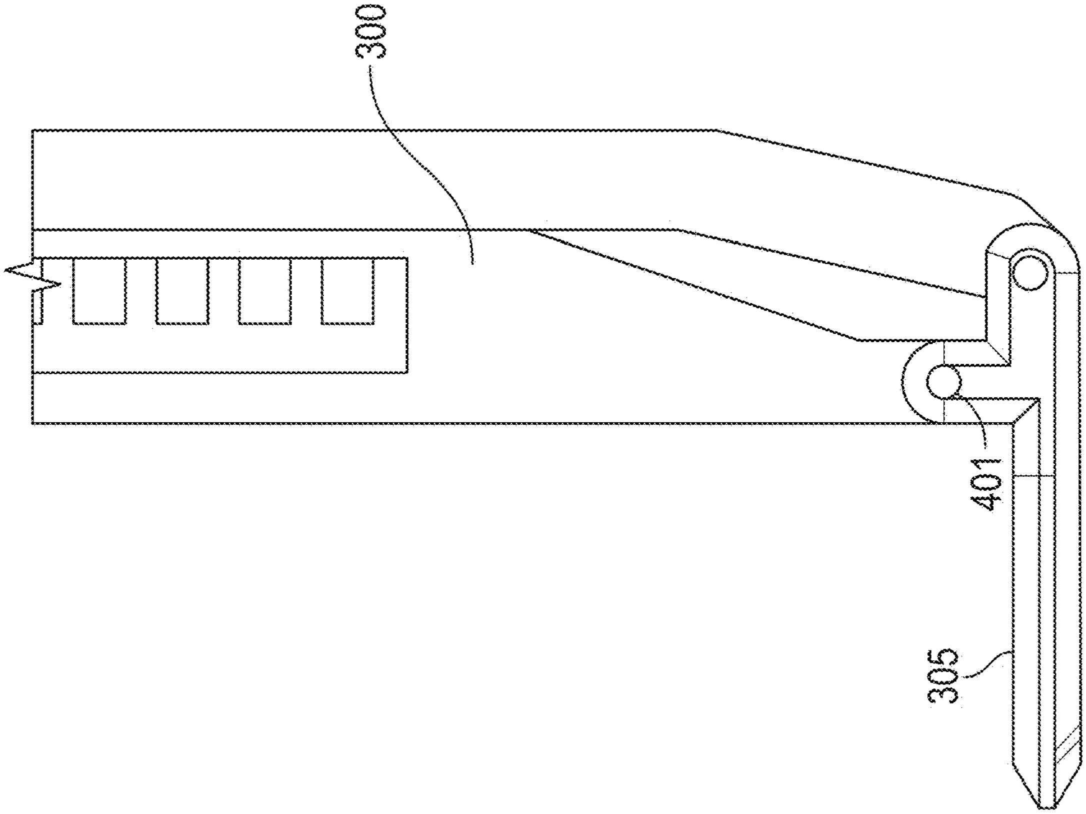
FIG. 5B depicts an enlarged side view of the distal end of the guard of FIG. 3.
Figure 5A:
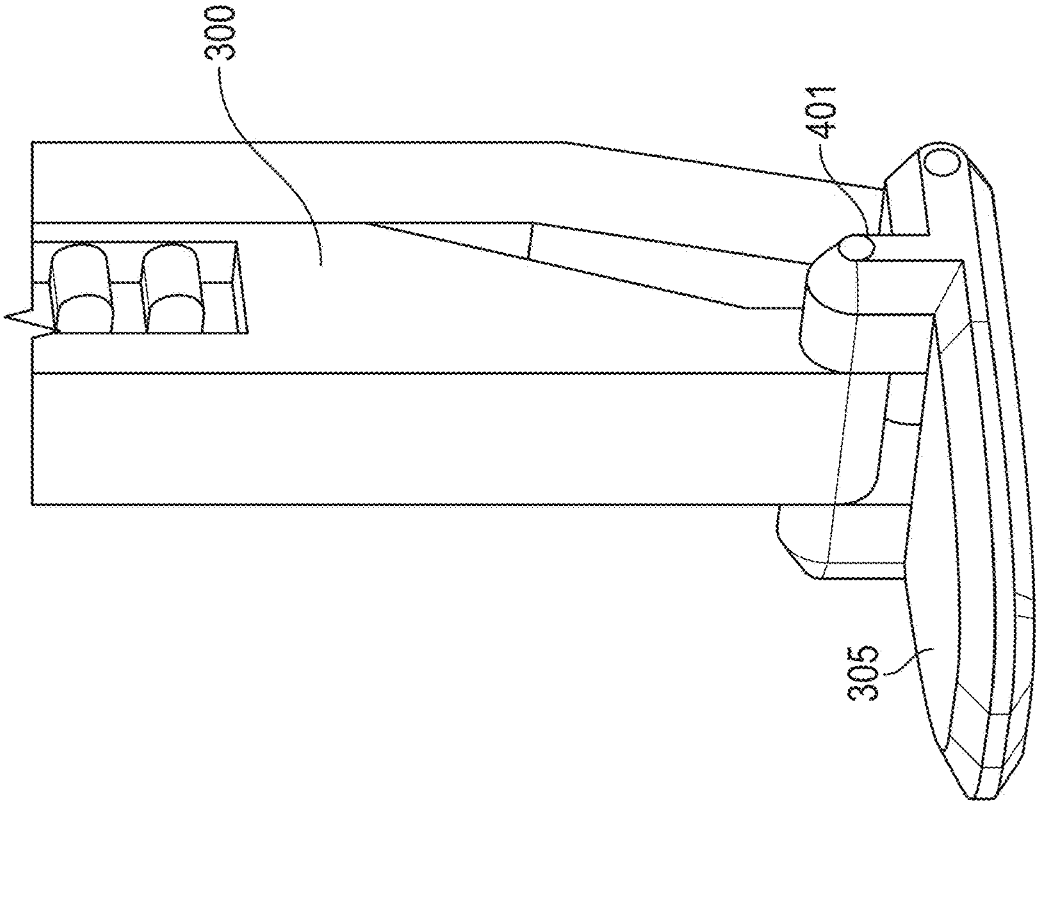
FIG. 5A depicts an enlarged perspective view of the distal end of the guard of FIG. 3.

Referring now to FIGS. 5A and 5B, the guard plate 305 is shown pivoted from the first position to a second pivoted position. In the second pivoted position, a longitudinal axis of the guard plate 305 may be perpendicular to or generally perpendicular to a longitudinal axis of the guard body 304. In certain embodiments, once the guard plate 305 is positioned proximate to the target anatomy, the doctor may twist the knob to cause the guard plate 305 to pivot to the second position so that the top surface 402 contacts the underside of the target anatomy. The guard plate 305 and/or the guard 300 may then be locked into place around the target anatomy.

In certain embodiments, the guard plate 305 may be pivoted to any angle between the extended position of FIG. 4A and a max pivot position, depending on the length and capabilities of the pivot mechanism present in the guard body 304.

Figure 6B:
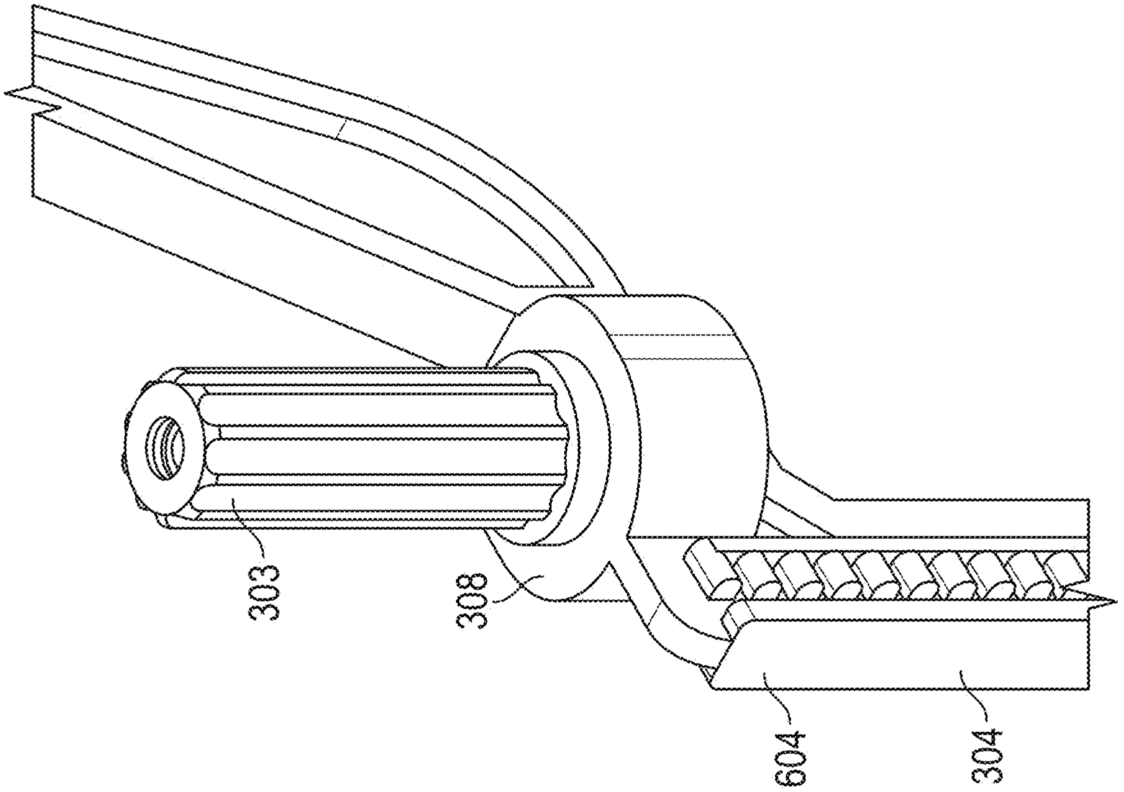
FIG. 6B depicts an enlarged perspective view of a proximal portion of the guard of FIG. 3.
Figure 6A:
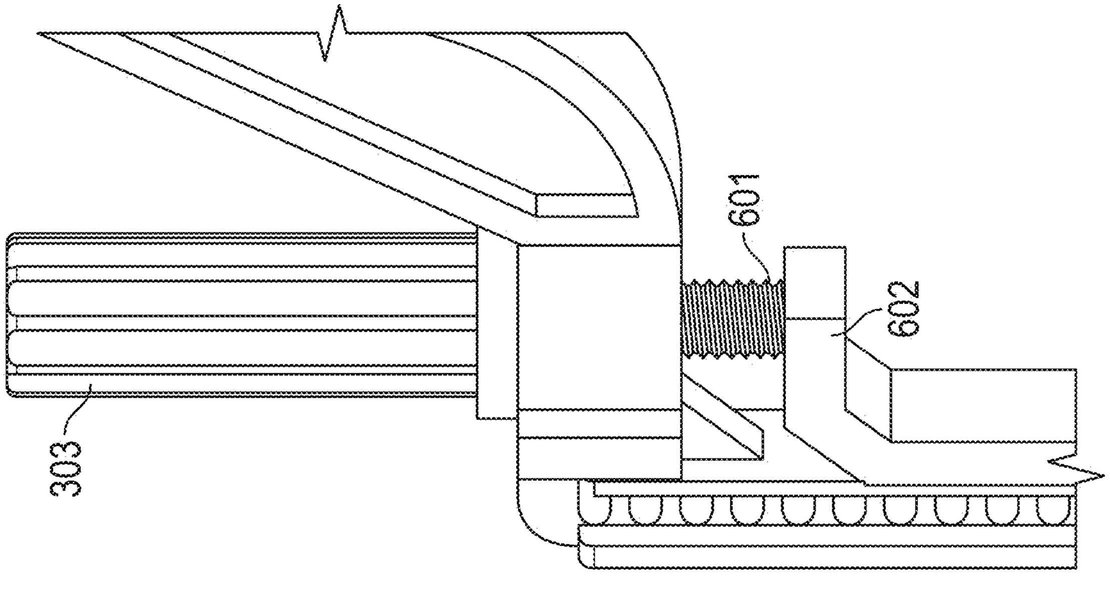
FIG. 6A depicts an enlarged side view of a proximal portion of the guard of FIG. 3.

Referring now to FIG. 6A, the knob 303 may be attached to a pivoting arm 602 by a knob screw 601. When the physician wants to change the angle of the guard plate 305, the physician may rotate the knob 303, which in turn rotates the knob screw 601, and causes the pivoting arm 602 to move towards the distal end of the guard. As the pivoting arm 602 moves toward the distal end, the top surface of the guard plate 305 pivots up towards the guard body 304. If the doctor rotates the knob 303 in the opposite direction, rotation of the knob screw 601 will cause the pivoting arm 602 to move towards the proximal end of the guard 300 and the top surface of the guard plate 305 to rotate away from the guard body 304.

In alternative embodiments, other control mechanisms (e.g., buttons, switches, triggers, levers, etc.) may be used to change the angle of the guard plate 305.

In some embodiments, the guard 300 may act as an instrument shuttle. As shown in FIG. 6B, the guard body 304 may contain a track 604. The track 604 can allow for additional instruments to couple to and advance along the guard 300 to the target area. For example, in certain embodiments, a working channel can be coupled to and advanced along the track 604. For example, once coupled, the working channel can be advanced to contact a side (e.g., top side) of the target area (e.g., the lamiae, facet, etc.) opposite the guard plate 305. The working channel can be secured on the opposite side from the guard plate 305 to provide a clear path to the target anatomy for the decompression procedure and/or provide further protection to the surrounding anatomy. In certain embodiments, the guard plate 305 may act as an engagement feature for engaging with or securing to the target anatomy to provide a stable and consistent path towards the target anatomy for instruments advancing along the guard 300 (e.g., via the track 604).

Figure 7A:
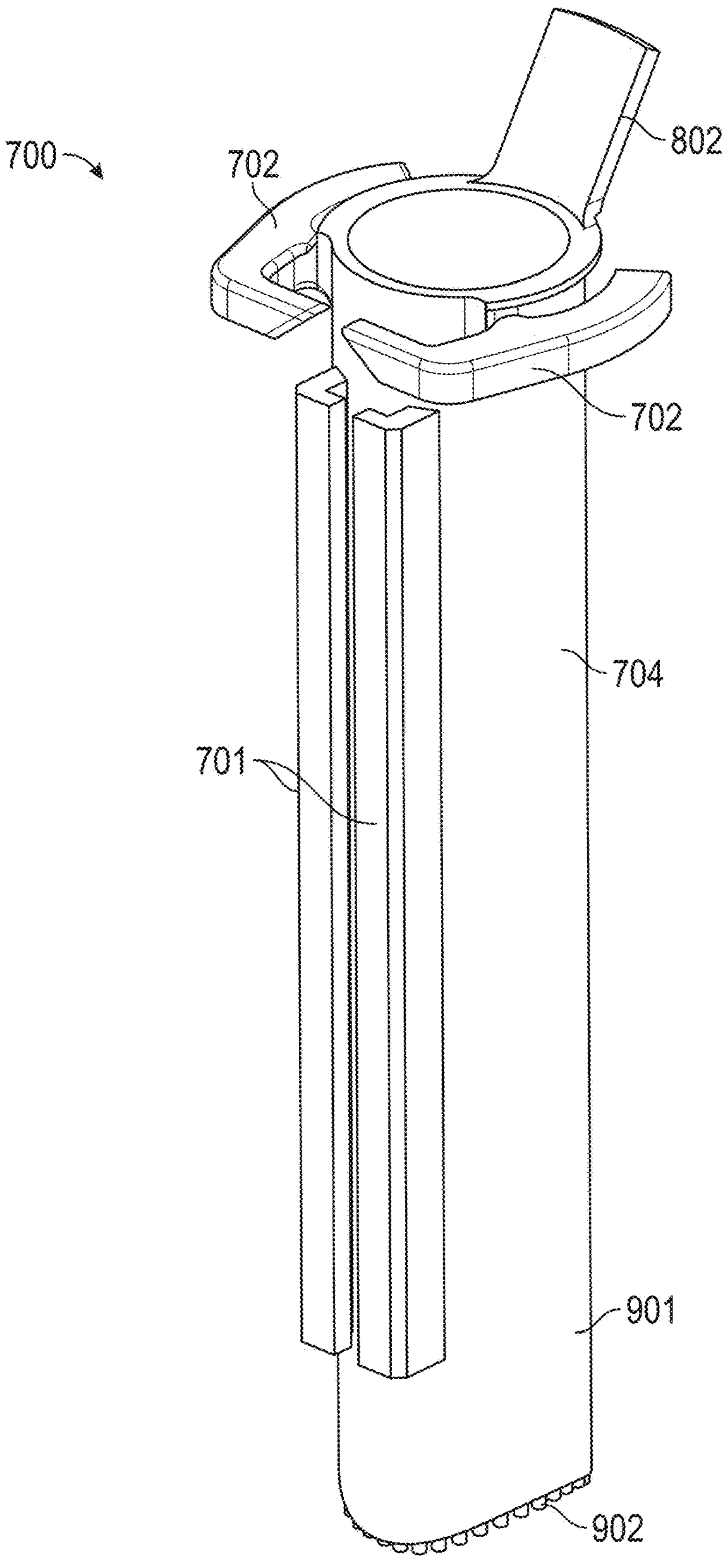
FIG. 7A depicts a perspective view of an embodiment of a working channel.
Figure 7B:
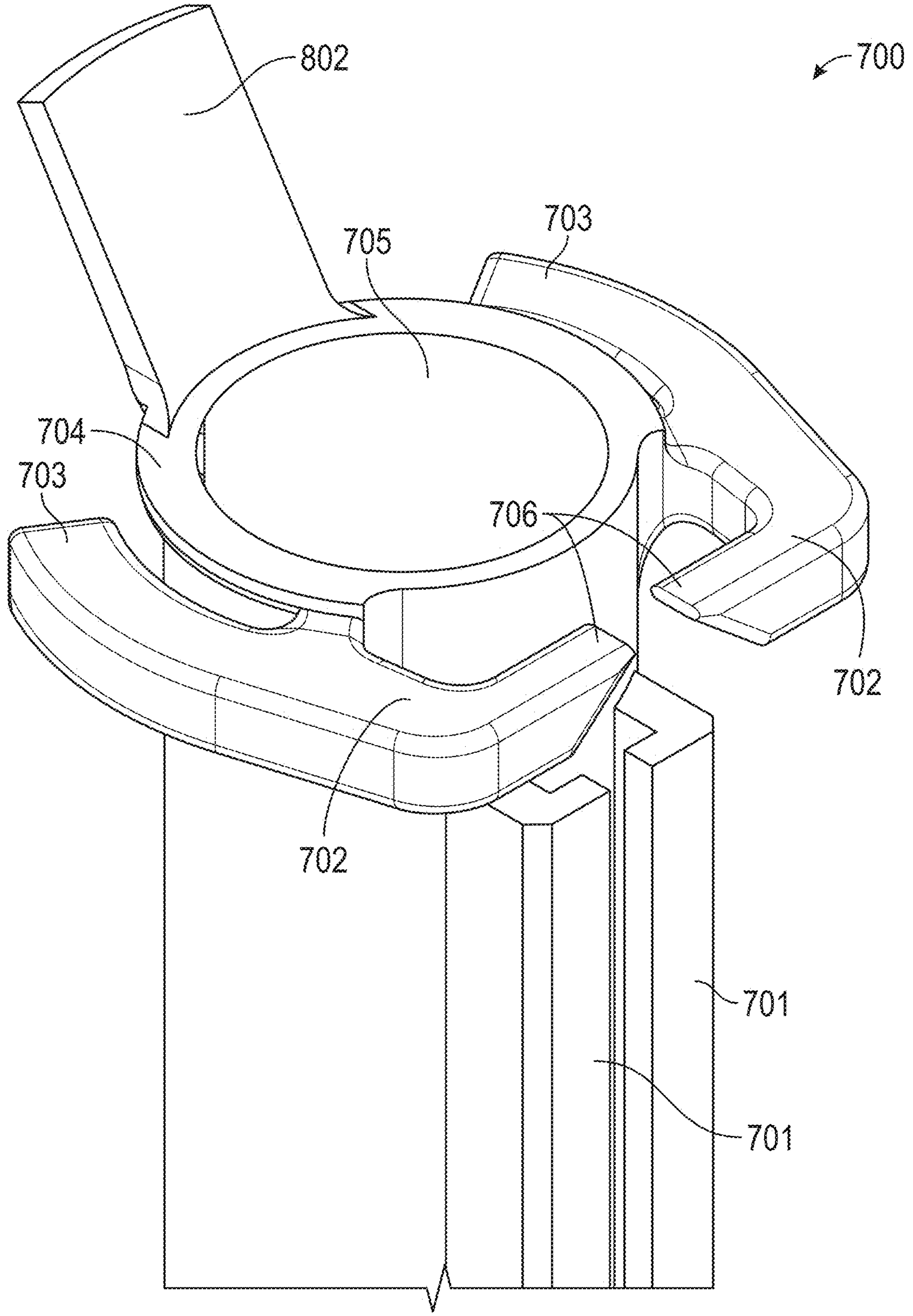
FIG. 7B depicts an enlarged perspective view of a proximal end of the working channel of FIG. 7A.

Referring to FIG. 7A, a perspective view of a working channel 700 is depicted. A perspective view of a proximal portion of the working channel 700 is depicted in FIG. 7B. In certain embodiments, the working channel 700 may have a channel body 704. The channel body 704 may be tubular or generally tubular in shape. One or more instruments may be advanced through the channel body 704 to the target area as further described herein. In some embodiments, the working channel 700 can be a dilator.

In certain embodiments, the working channel 700 can include a track coupler 701 extending down an external length of the channel body 704. The track coupler 701 may couple with the track 604.

Figure 8B:
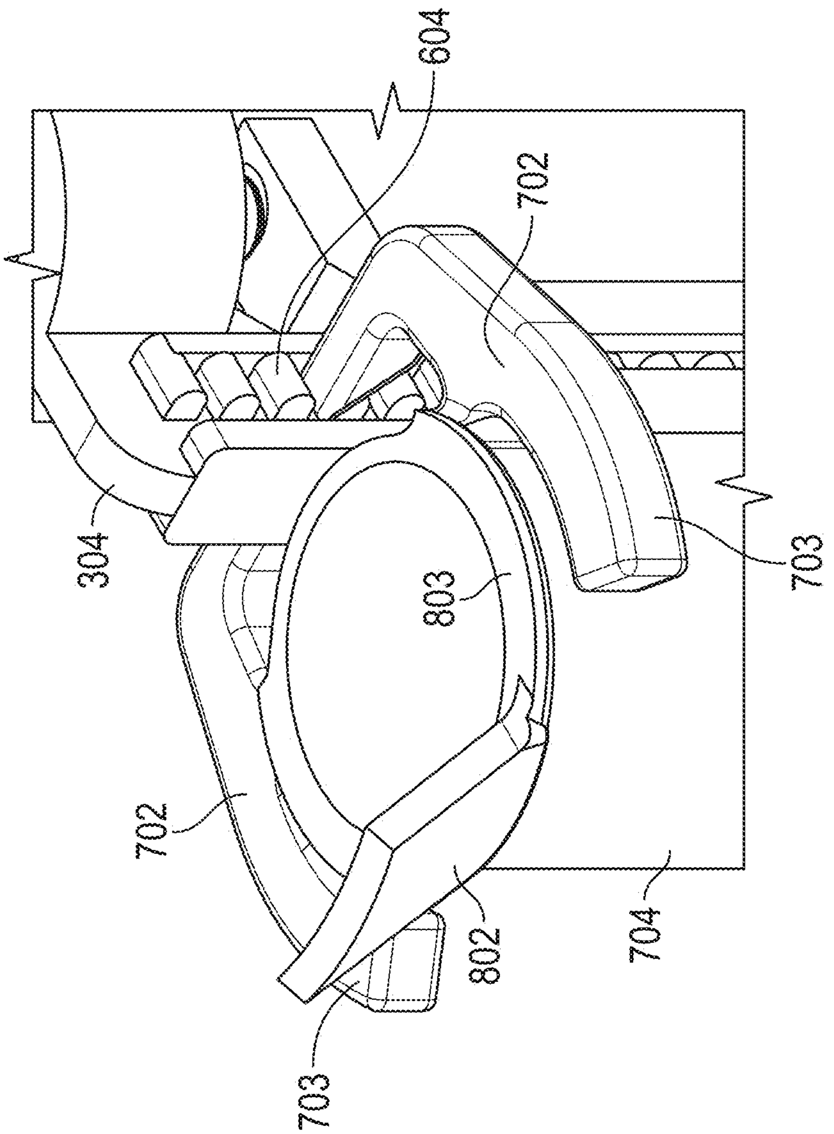
FIG. 8B depicts an enlarged perspective view of a proximal portion of the decompression system of FIG. 8A.
Figure 8A:
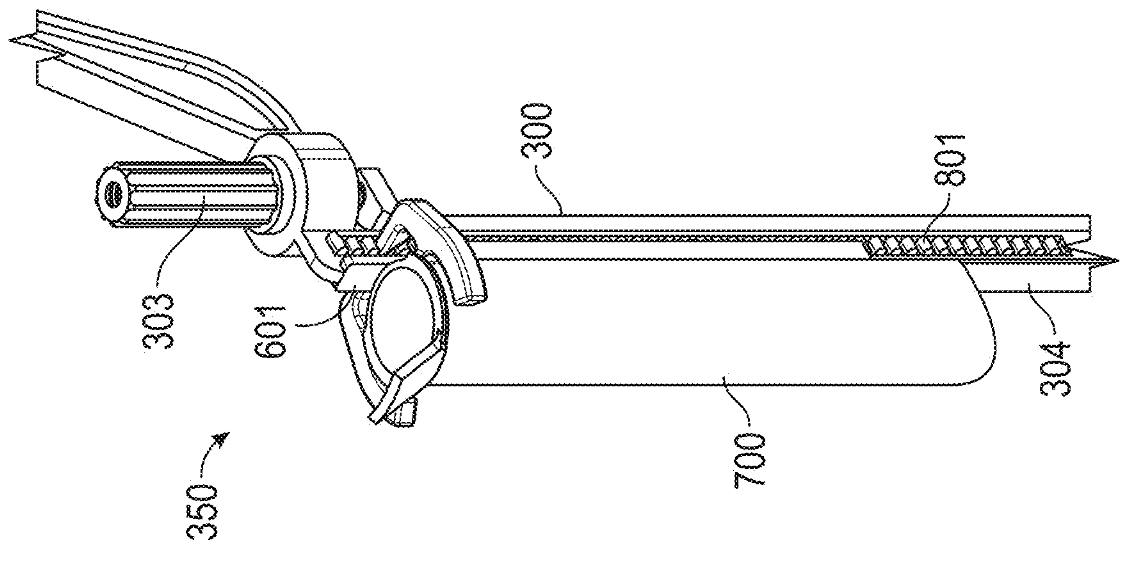
FIG. 8A depicts a perspective view of a portion of a decompression system including the guard of FIG. 3 and the working channel of FIG. 7A.

As shown in FIG. 8A, in some embodiments, the track 604 can include a plurality of grooves 801. The grooves 801 may allow for additional instruments to couple to and advance along the track 604. In some embodiments, the grooves 801 may be alternating male and female grooves that allow an instrument (e.g., the working channel 700) to engage the track 604 and releasably secure to a fixed position along the track 604 (e.g., when not advancing or retracting along the track 604 as described herein). The working channel 700 can be releasably secured to the track 604 to prevent unintended retraction and/or advancement.

In certain embodiments, the working channel 700 and guard 300 can together form a guide system or decompression system 350. As described herein, the decompression system 350 can engage a target area and protect the surrounding anatomy while acting as a guide for additional instruments for a decompression procedure.

The working channel 700 can include track coupling arms 702 configured to engage with the track grooves 801 of the track 604. In certain embodiments, two track arms 702 may be positioned around an opening 705 of the channel body 704. The track arms 702 can provide a locking mechanism for releasably fixing a positioning the working channel 700 along the track 604. For example, in certain embodiments, ends or tips 706 of the track arms 702 can engage the grooves 801 to fix the position of the working channel 700 along the track 604, as shown for example in FIGS. 8A-8B. The tips 706 can be male engagement members configured to engage with female grooves 801 of the track 604. In certain embodiments, open ends 703 of the track arms 702 may be manually pinched inward toward the opening 705 of the channel body 704 so that tips 706 of the track arms 702 spread apart and release from the grooves 801. In the pinched position, the working channel 700 can be advanced along the track. When the open ends 703 are released, the tips 706 of the arms can engage the grooves 801 and the working channel 700 can be locked or secured into place. The grooves 801 may serve as a series of fixed positions to which the working channel may fix.

Referring to FIG. 8B, a magnified view of the working channel 700 coupled to the guard body 304 via the track 604 is depicted. A lip 802 may protrude from the top surface 803 of the channel body 704. In some embodiments, one or two light sources may be affixed to the lip 802 to improve visibility around the surgical site. Lights may be disposable or reusable and affixed to the lip 802 through clips or other fastening mechanisms. In other embodiments, loupes or a microscope may be coupled to the lip 802 to facilitate visualization of the surgical site.

Figure 9A:
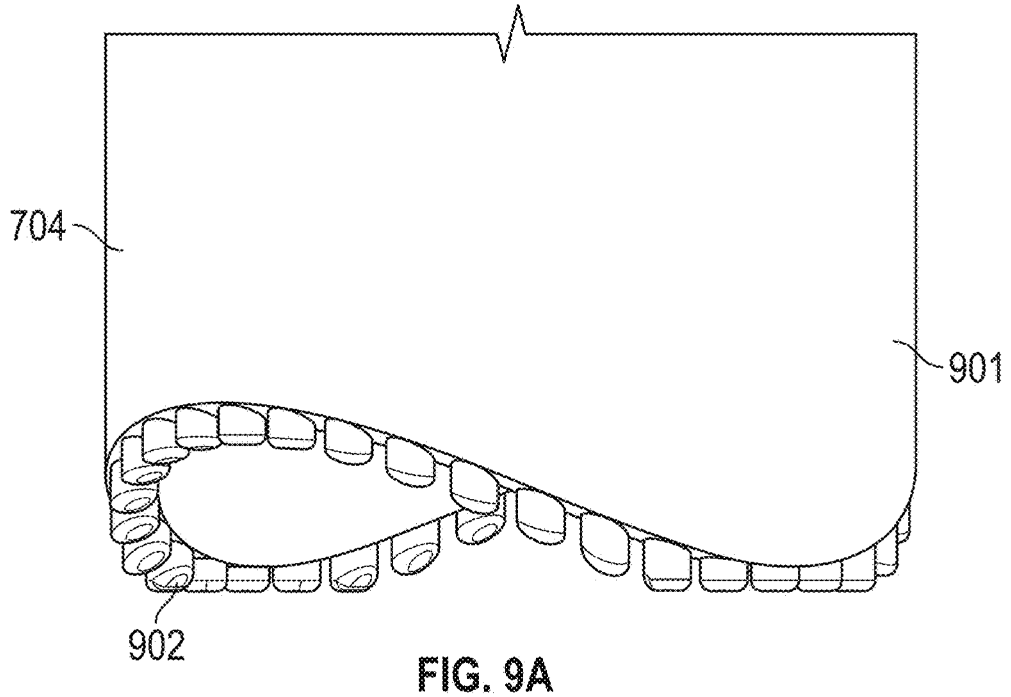
FIG. 9A depicts an enlarged side view of a distal end of the working channel of FIG. 7A.
Figure 9B:
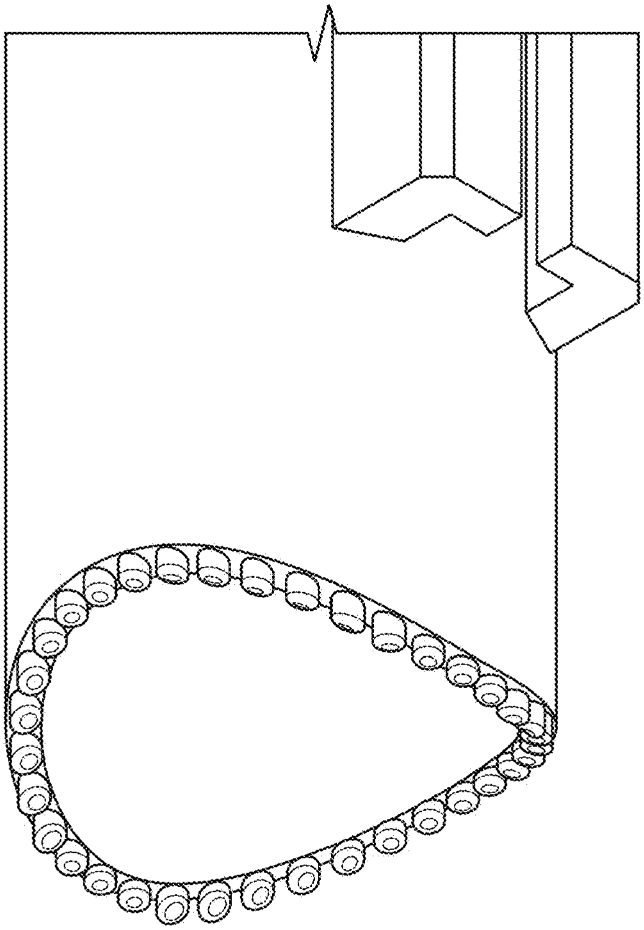
FIG. 9B depicts an enlarged perspective view of the distal end of the working channel of FIG. 7A.

FIG. 9A and FIG. 9B depict a distal end 901 of the channel body 704. The distal end 901 may contact a side of the target area opposite of the guide plate 305. In certain embodiments, the distal end 901 of the channel body 704 can include one or more surface features 902. The surface features 902 may be protrusions or teeth to prevent slipping when positioned against bone. In some embodiments, the surface features 902 can be rough, abrasive, or otherwise textured surfaces to prevent slipping when positioned against the bone. In some embodiments, the surface features 902 may be a non-slip material.

The distal end 901 may be irregular (e.g., not flat), to better grip the bone. In certain embodiments, the distal end 901 may be concave and/or convex in shape to match the shape of the target area (e.g., the lamina).

The surface features 902 may vary in number and be various shapes and dimensions depending on the application. For example, in some embodiments, the working channel 700 may contain no surface features at the distal end.

In certain embodiments, the working channel may be between 30 mm and 120 mm in length. In certain embodiments, working channels of various lengths can be provided to accommodate different medical instruments.

Figure 10:
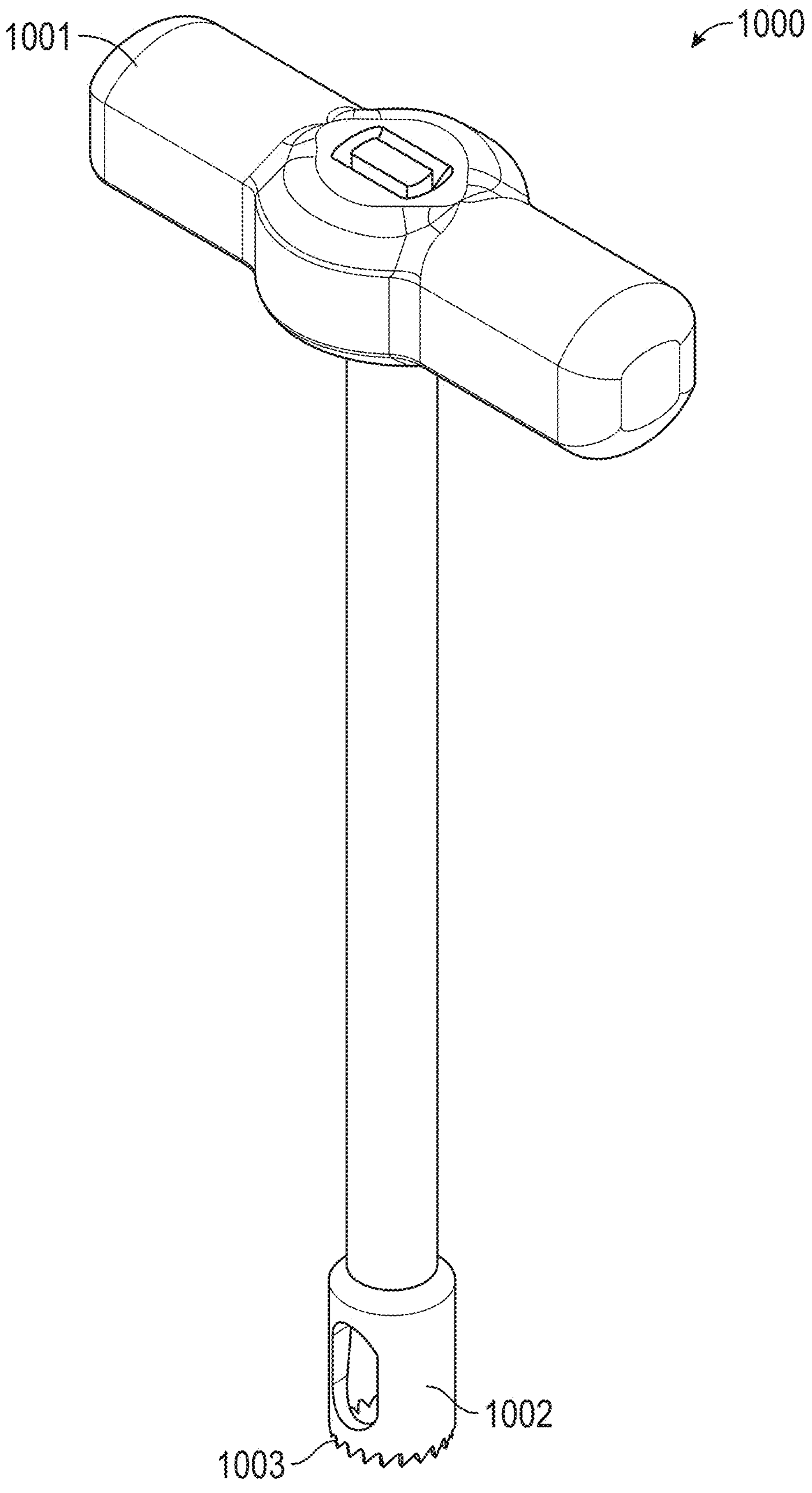
FIG. 10 depicts a perspective view of an embodiment of a trephine.
Figure 11A:
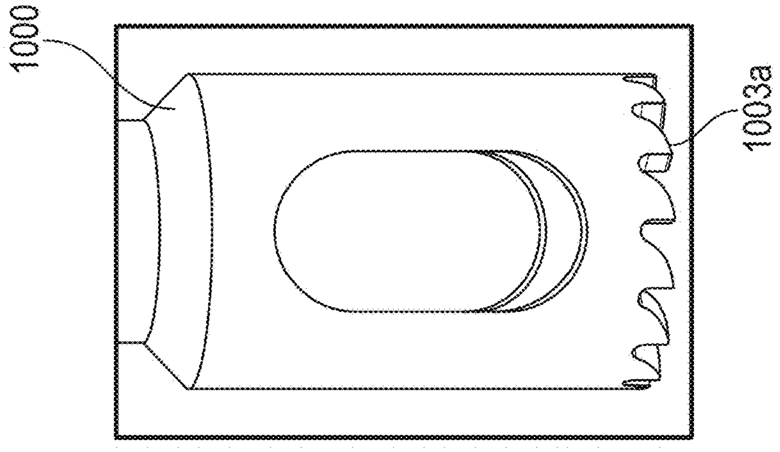
FIG. 11A depicts an enlarged side view of an embodiment of a distal end of the trephine of FIG. 10.
Figure 11B:
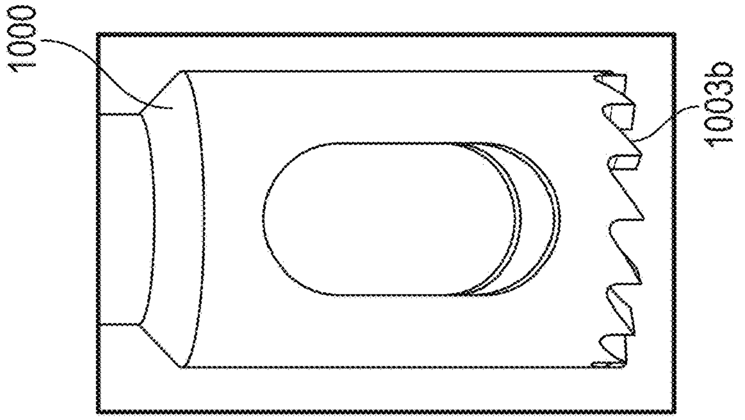
FIG. 11B depicts an enlarged side view of an embodiment of a distal end of the trephine of FIG. 10.
Figure 11C:
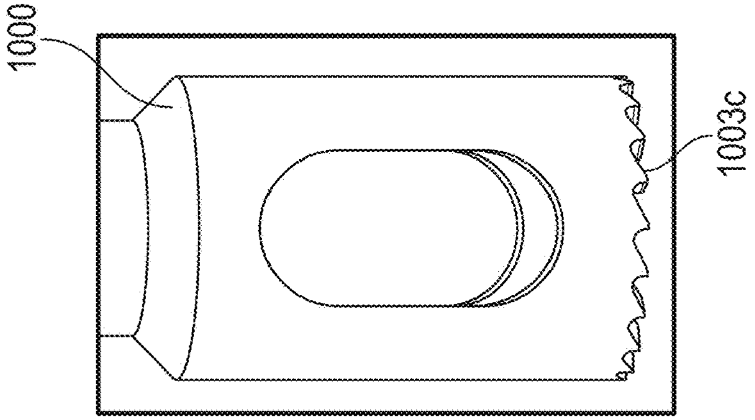
FIG. 11C depicts an enlarged side view of an embodiment of a distal end of the trephine of FIG. 10.
Figure 11D:
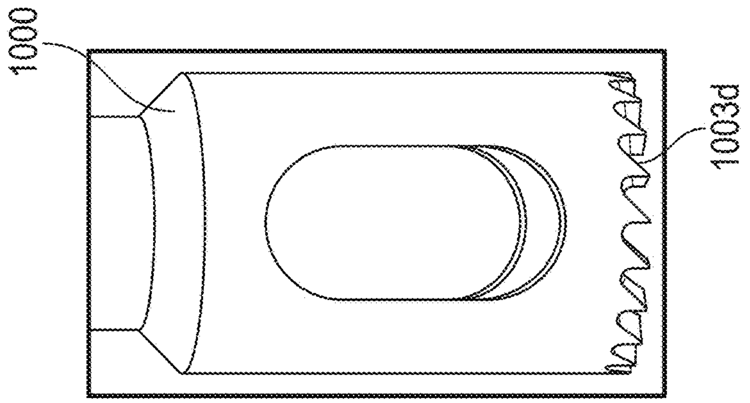
FIG. 11D depicts an enlarged side view of an embodiment of a distal end of the trephine of FIG. 10.

Referring to FIG. 10, in certain embodiments a trephine 1000 may be advanced down the working channel 700 to the target area. After advancing the trephine 1000 to the target area, the trephine 1000 can be used to remove at least part of the bone (and/or other target anatomy) at the target area. For example, after the trephine 1000 is advanced to the target area, the trephine 1000 may be rotated around a longitudinal axis through the center of the trephine 1000 by gripping and rotating a handle 1001. In certain embodiments, the trephine 1000 can be rotated back and forth to create a cutting effect. The distal end 1002 of the trephine 1000 can contain a cutting edge 1003. The cutting edge may include one or more cutting features, such as teeth. As the trephine 1000 is rotated and cuts into the bone, the cut bone can become lodged in the distal end 1002 of the trephine. In certain embodiments, the trephine 1000 can be used to cut through the bone at the target area until it contacts the guard plate 305 on the opposite or bottom side of the target anatomy. As described herein, the guard plate 305 can act as a safety stop to prevent nerve, spinal cord, or surrounding anatomy damage by the trephine 1000. After the trephine 1000 contacts the guard plate 305, the trephine 1000 can be withdrawn and removed from the working channel 700. Removal of the bone at the target area can create the desired space to treat the spinal stenosis.

Once the trephine 1000 is withdrawn, the working channel 700 may provide visibility for a doctor to see if more bone or tissue, such as ligamentum flavum, needs to be removed.

Other medical devices may be inserted down the working channel 700 in addition to or alternatively to the trephine 1000, such as a drill, kerrison, burr, or other instrument to cut or alter the target anatomy as desired. In some embodiments, several different medical devices may be used in succession in conjunction with the working channel 700. For example, in certain embodiments, different devices may be used to perform different steps of a procedure or to achieve different results. For example, if more tissue or bone needs to be removed after use of the trephine 1000, the doctor may use a kerrison or pituitary subsequently to debulk the target anatomy.

As illustrated in FIGS. 11A through 11D, the trephine 1000 may have different types of cutting edges 1003*a-d* present at the distal end. The cutting edges may contain teeth that are wider or shallower depending on the desired cutting effect. In certain embodiments, the teeth may be angled at different degrees to accommodate different portions of the spine. For example, a trephine with teeth angled at a first angle may be used for the L3 and L4 spinal motion segments while a trephine with teeth angled at a second angle may be used for the L4 and L5 spinal motion segments. In some embodiments, the teeth may be sharper, more curved, or cut in a specific pattern to achieve a desired cutting effect. In some embodiments, the trephine may not contain teeth at the distal end and may have some other feature to alter the target anatomy. In certain embodiments, a plurality of trephines may be provided having different cutting edges for use on different anatomies, at different locations, and/or for different cutting effects.

Figure 12:
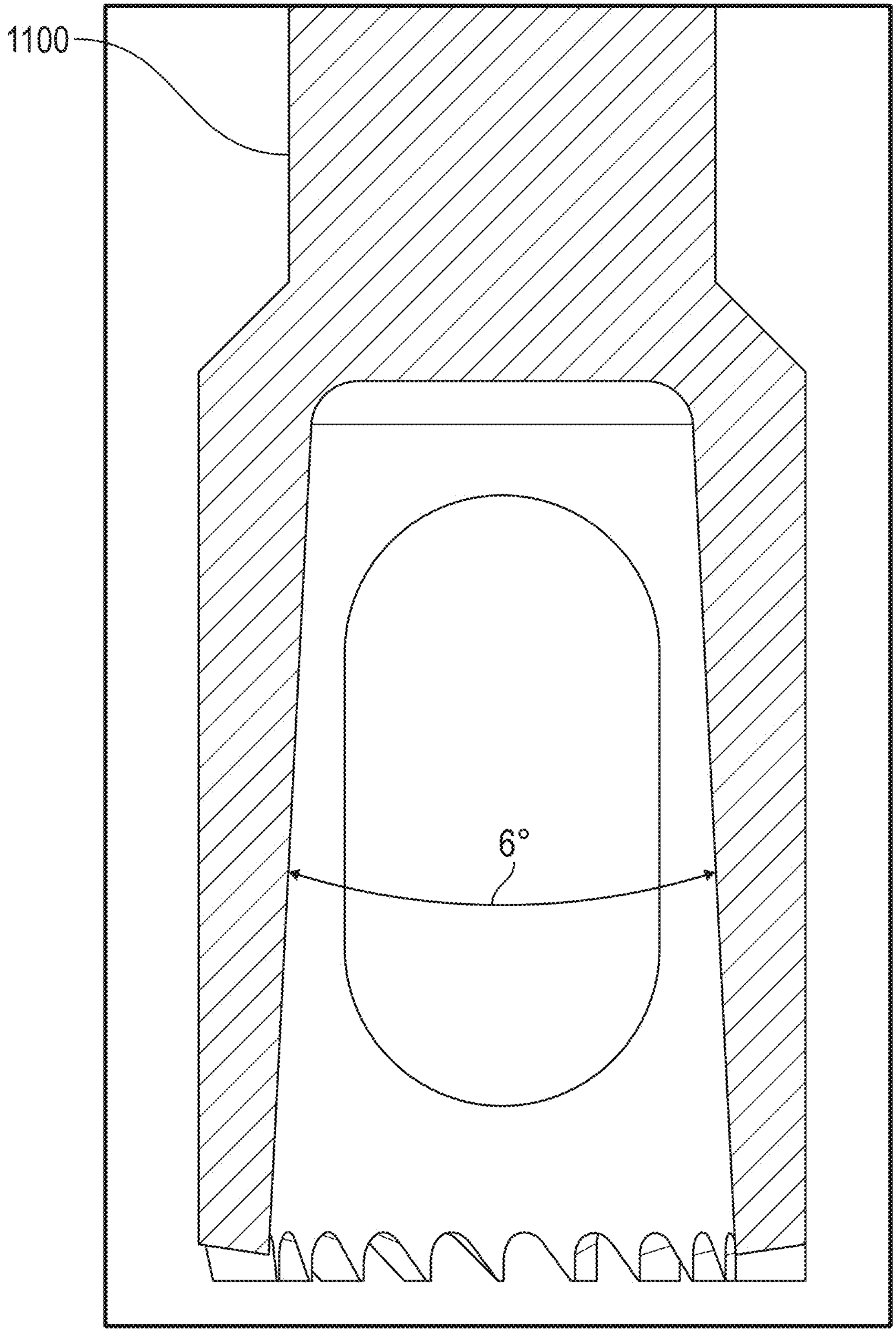
FIG. 12 depicts an enlarged cross-sectional view of the distal end of the trephine of FIG. 10.

FIG. 12 illustrates a cross-sectional view of the trephine 1000. As shown, a conical angle of the depicted trephine is 6°. However in alternative embodiments, the angle may be more or less than 6 degrees (e.g., between 1 degree and 36 degrees, 2 degrees and 18 degrees, or any other suitable angle). As the conical angle changes, the overall size of the distal end of the trephine changes, and consequently, the amount of bone removed.

In some embodiments, after the desired amount of bone is removed, the working channel 700 may be detached from the guard 300, then the guard 300 removed from the surgical site.

Figure 13A:
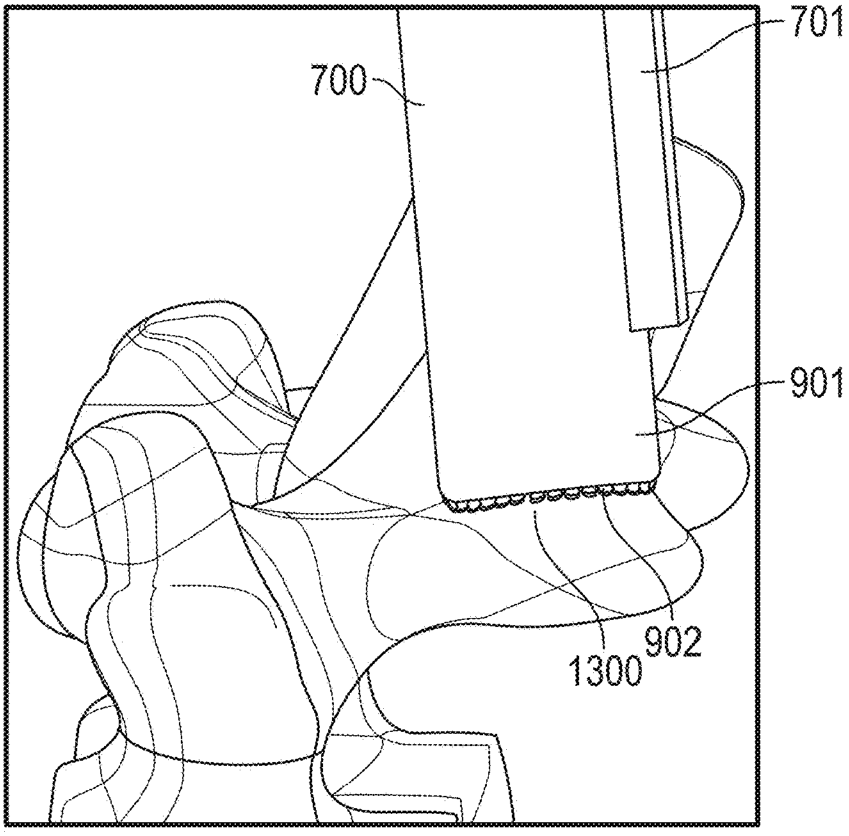
FIG. 13A depicts an example of the working channel of FIG. 7A positioned adjacent to a target anatomy for a decompression procedure.

FIG. 13A illustrates an example of the distal end 901 of the working channel 700 in contact with target anatomy 1300. In certain embodiments for example, the target anatomy 1300 may be a lamina in the spine, as shown in FIG. 13A. The features 902 protruding from the proximal end may contact the bone or tissue at the target anatomy 1300. As previously indicated, the features 902 may be specifically configured (e.g., shaped, dimensioned, or composed of a certain material) so that the features 902 grip onto the target anatomy 1300. Additionally, the distal end 901 may be contoured to align with the specific shape of the target anatomy 1300. In certain embodiments, the working channel 700 may be positioned at other areas or sides of the target anatomy 1300 than those illustrated in FIG. 13A.

Figure 13B:
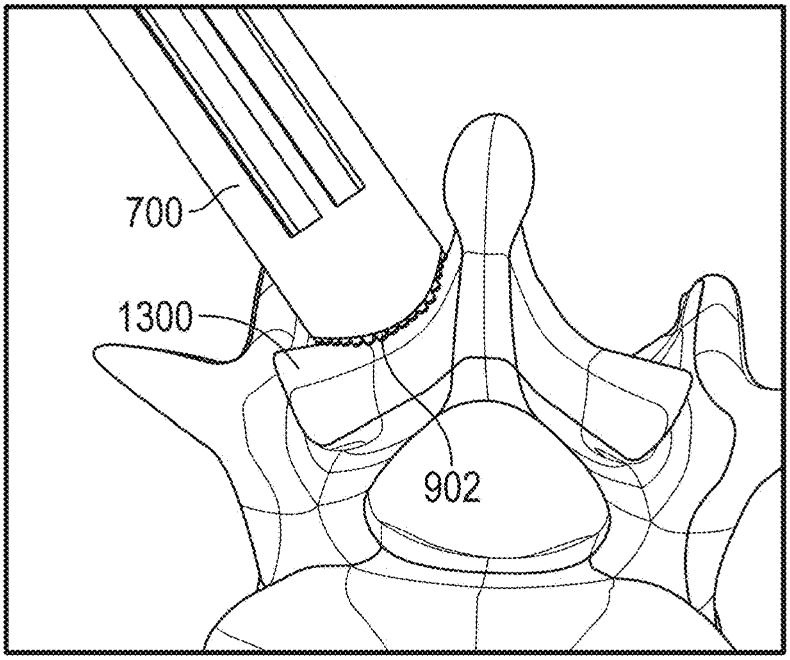
FIG. 13B depicts an example of the working channel of FIG. 7A positioned adjacent to the target anatomy.

FIG. 13B illustrates an alternative angle of the working channel 700 contacting the target anatomy 1300. In some embodiments, the distal end 901 of the working channel 700 may be sloped or curved to nest into the target anatomy 1300 (e.g., the lamina in FIG. 13B). In certain embodiments, the distal end 901 may be shaped so that the features 902 make contact with the target anatomy. In some embodiments, only some of the features 902 may contact the target anatomy.

Figure 14A:
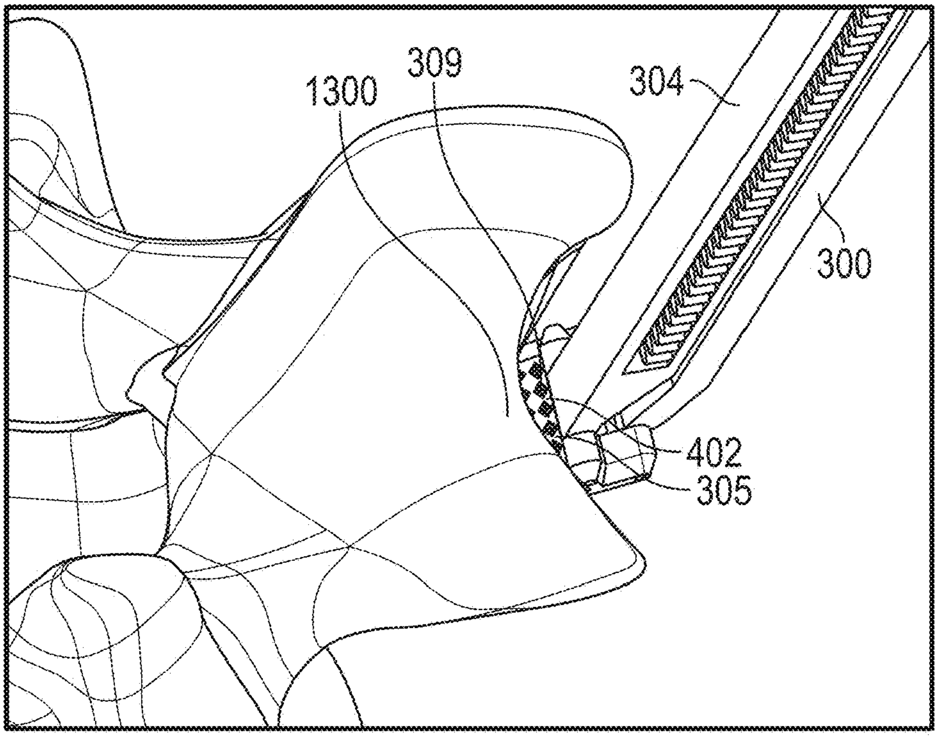
FIG. 14A depicts an example of the guard of FIG. 3 positioned adjacent to the target anatomy.

FIG. 14A illustrates the guard 300 positioned against the target anatomy 1300. As shown in FIG. 14A, the target anatomy 1300 may be a lamina. As previously described, the guard plate 305 may be positioned against the target anatomy 1300. When the guard plate 305 is positioned against the target anatomy 1300, the guard plate may minimize movement of the guard 300 in at least some directions. The guard plate 305 may contain surface features 309 on the top surface 402. The surface features 309 may be protrusions or teeth to prevent slipping when positioned against bone. In some embodiments, the surface features 309 can be rough, abrasive, or otherwise textured surfaces to prevent slipping when positioned against the bone. In some embodiments, the surface features 309 may be a non-slip material. The surface features 309 can improve the grip and surface contact with the target anatomy. In certain embodiments, the surface features 309 can act as engagement features for engaging with or securing to the target anatomy to provide a stable and consistent path towards the target anatomy for instruments advancing along the guard 300 (e.g., via the track 604). In alternative embodiments, the guard 300 and guard plate 305 may be positioned at other areas along the target anatomy.

Figure 14B:
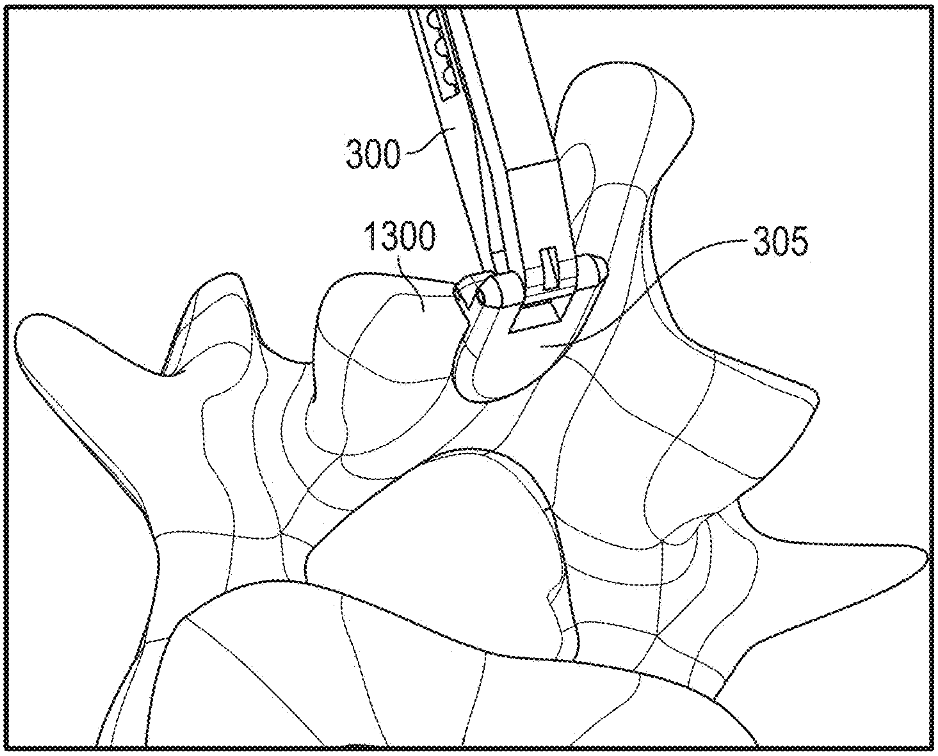
FIG. 14B depicts an example of the guard of FIG. 3 positioned adjacent to the target anatomy.

Referring to FIG. 14B, another angle of the guard 300 positioned against the target anatomy 1300 is illustrated. The bottom of the guard plate 305 may be unobstructed as the top surface of the plate contacts the bottom of the target anatomy 1300.

Figure 15A:
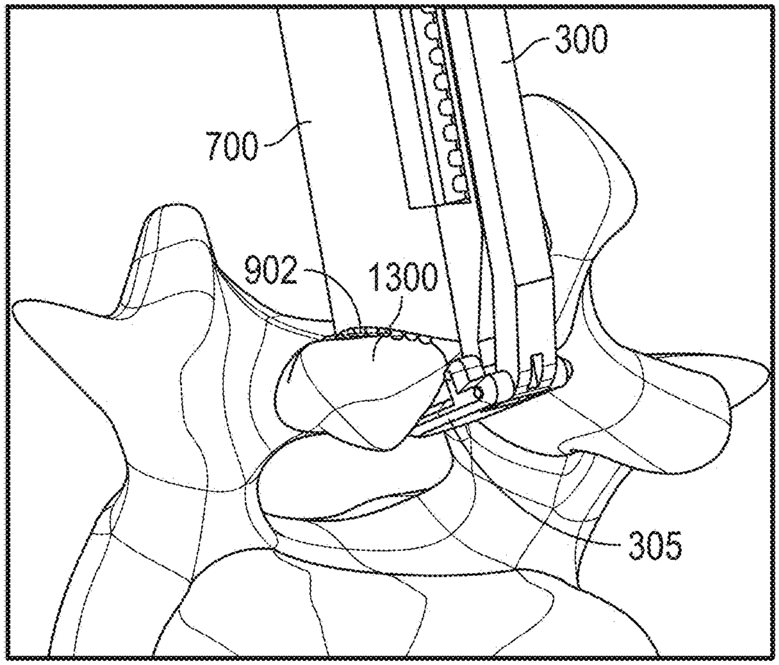
FIG. 15A depicts an example of the decompression system of FIG. 8A positioned adjacent the target anatomy.

FIG. 15A illustrates the guard 300 coupled to the working channel 700 positioned against the target anatomy 1300. In certain embodiments, the target anatomy 1300 may be clamped between the distal end 901 of the working channel 700 and the top surface 402 of the guard plate 305. For example, in some embodiments, the target anatomy 1300 can be clamped between the surface features 902 and the surface features 309. When the guard 300 and working channel 700 are positioned, the working channel 700 can provide a path for other surgical tools to align with and access the target anatomy 1300. Additionally, the guard 300 and working channel 700 may protect surrounding anatomy from contact or damage during the surgical procedure. Using the guard in conjunction with the working channel during a procedure may provide support and alignment for other surgical tools.

Figure 15B:
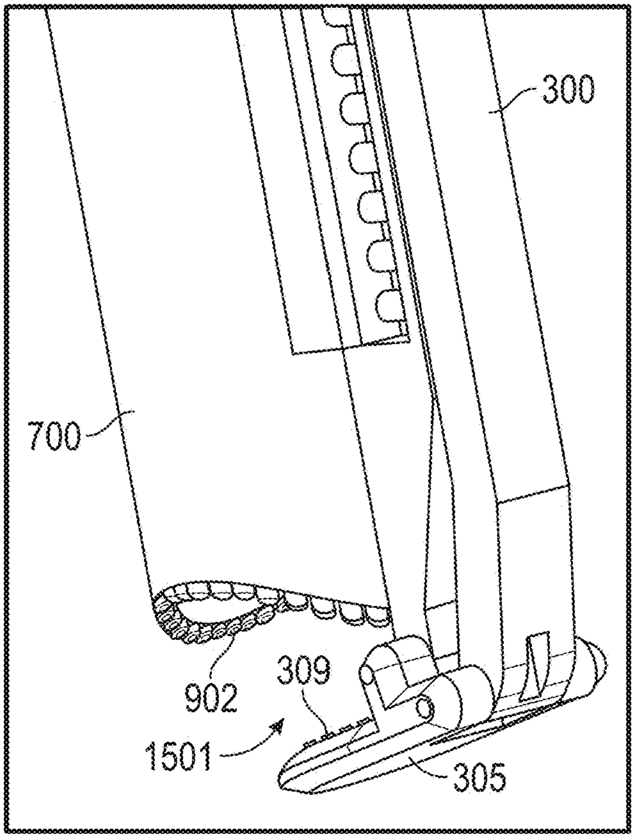
FIG. 15B depicts a perspective view of a distal end of the decompression system of FIG. 8A.

FIG. 15B illustrates the guard 300 coupled to the working channel 700, as illustrated in FIG. 15A, but without the target anatomy 1300. FIG. 15B shows a space 1501 between the top of the plate 305 and the features 902 of the working channel 700. The space 1501 can be increased or decreased by moving the working channel 700 proximally or distally, respectively, along the track 604.

Figure 16:
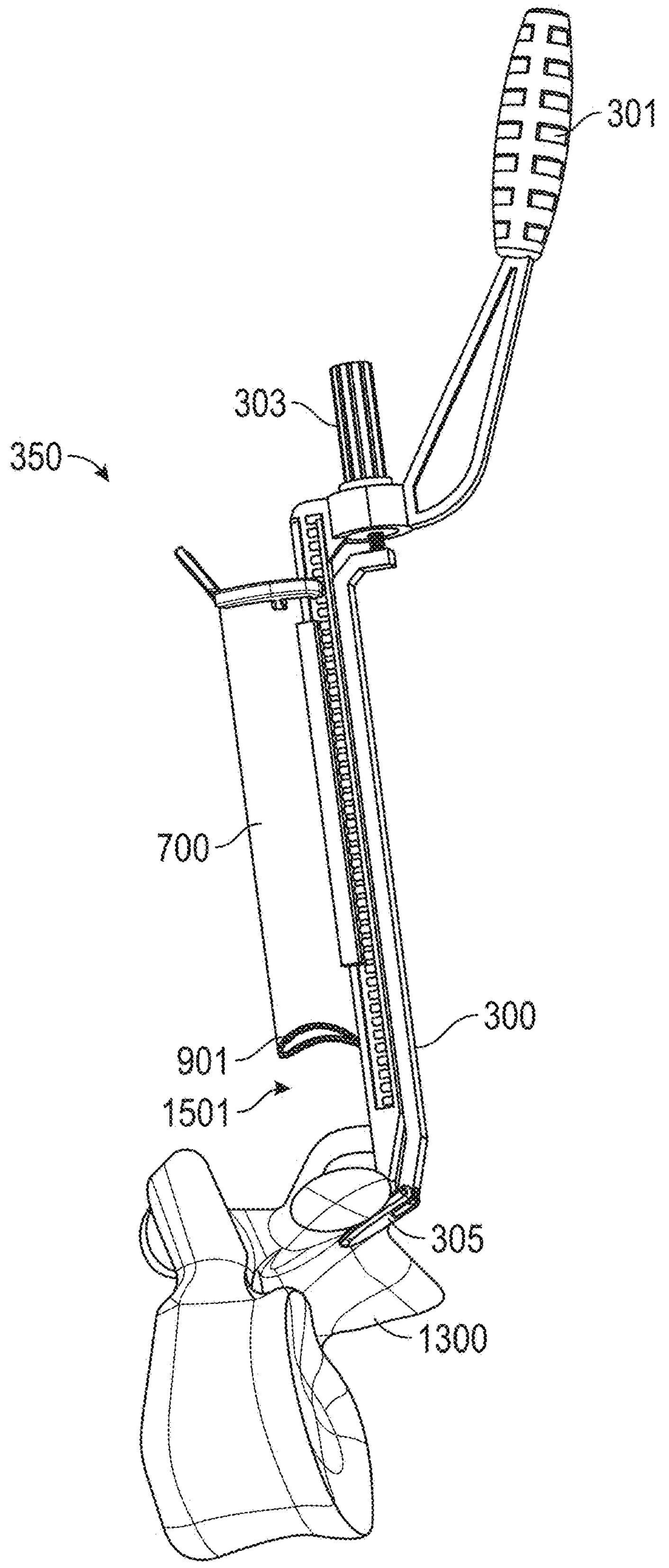
FIG. 16 depicts a perspective view of the decompression system of FIG. 8A positioned adjacent to the target anatomy.

FIG. 16 illustrates the guard 300 coupled to the working channel 700 and positioned around the target anatomy 1300. As shown in FIG. 16, the working channel 700 is positioned so that the distal end 901 is spaced apart from the target anatomy 1300. As shown in FIG. 16, the guard plate 305 is positioned in contact with one side (e.g., the underside) of the target anatomy 1300. The working channel 700 may be lowered (e.g., advanced distally along the track 604) so that the space 1501 between the distal end 901 and the guard plate 305, and consequently the space between the distal end 901 and the target anatomy, decreases. The working channel 700 may be lowered until it contacts the opposite side (e.g., the top side) of the target anatomy 1300 from the guard plate 305. Lowering the working channel 700 into contact with the target anatomy 1300 may clamp the target anatomy between the working channel and the guard plate 305. In some embodiments, the working channel 700 may be lowered to squeeze the target anatomy (e.g., the lamina) between the working channel 700 and the guard plate 305. As shown in FIG. 16, the target anatomy may be a lamina of a patient.

As described with respect to FIGS. 8A-8B, in some embodiments the working channel 700 can be positioned at the target anatomy 1300 by maintaining the track arms 702 in an open configuration (e.g., by pinching the open ends 703), advancing the working channel 700 to contact the target anatomy 1300, and transitioning the track arms 702 to a closed configuration (e.g., by releasing the open ends 703) so that the track arms 702 engage the grooves 801 (e.g., via the tips 706) to secure the position of the working channel 700 along the track 604 and/or relative to the target anatomy 1300.

Figure 17A:
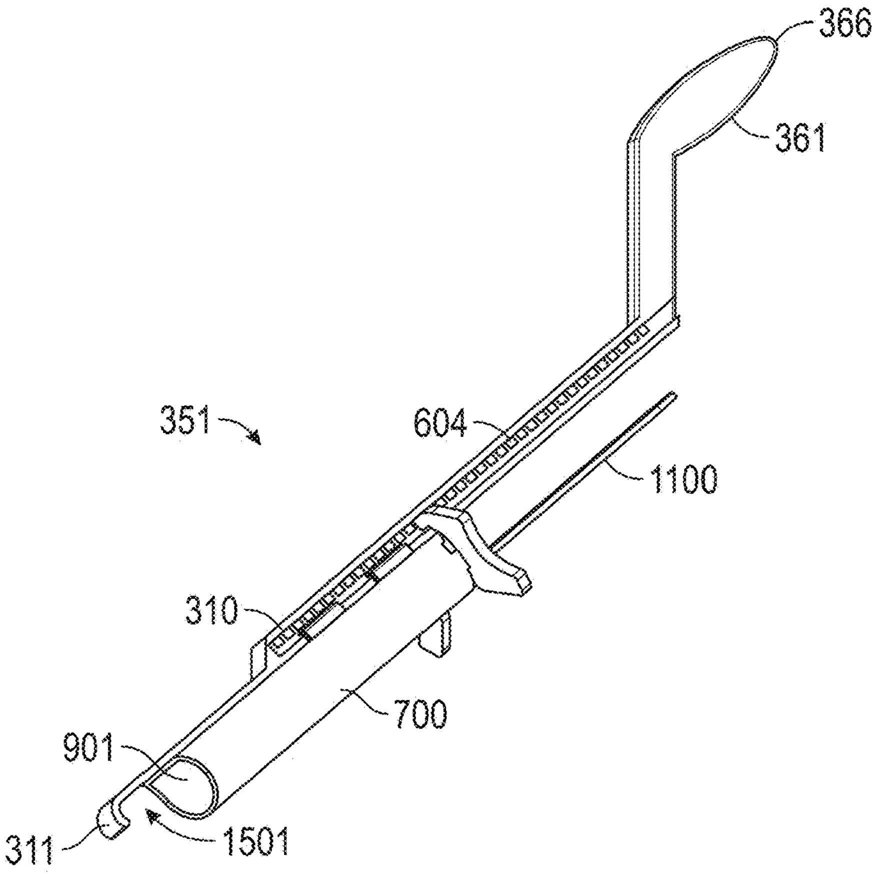
FIG. 17A depicts a perspective view of an embodiment of a decompression system.

FIG. 17A depicts another embodiment of a guide system or decompression system 351 that may be used in a surgical procedure. As shown in FIG. 17A, in some embodiments, the decompression system 351 can include an instrument shuttle 310. The instrument shuttle 310 can include features, such as a track, for coupling to additional instruments (such as a working channel) and advancing the additional instruments to the target area. For example, the instrument shuttle 310 may include a track 604, which may have any of the same and/or similar features and/or functions as the track 604 of the guard 300 and vice versa.

A proximal end 366 of the instrument shuttle 310 can include a handle 361 for manipulation by a user (e.g., a physician). The instrument shuttle 310 may be manipulated by the handle 361 to rotate and/or translate the instrument shuttle 310. For example, the handle 361 may be manipulated to maneuver the instrument shuttle 310 through muscle and other tissue.

In some embodiments, the decompression system 351 can include the working channel 700. The working channel 700 can couple to the instrument shuttle 310.

In certain embodiments, working channel 700 may advance up and down the instrument shuttle 310 to adjust the space 1501 between the distal end 901 of the working channel 700 and the target anatomy.

In some embodiments, the instrument shuttle 310 may have a hook 311 at its distal end. The hook 311 may be advantageous in procedures approaching inferior to the lamina. The hook 311 may be various sizes to easily couple to different sized or shaped bones. The hook 311 can engage with and/or secure to the target area or anatomy adjacent the target area. The hook 311 may secure the instrument shuttle 310 to provide a stable and consistent path towards to the target area for instruments advancing along the instrument shuttle 310.

In some embodiments, instrument shuttle 310 serves as a docking device for aligning the working channel 700 or other instrument coupled to the instrument shuttle 310. The hook 311 can be positioned under and contact (e.g., be slid under) that target anatomy at a fixed angle. Once the hook 311 is positioned on the desired bone, the working channel 700 may be advanced down the track 604. The target anatomy can be positioned between the distal end 901 of the working channel 700 and the hook 311. While a hook 311 is described with respect to the instrument shuttle 310, in certain embodiments, the instrument shuttle 310 may have alternative and/or additional engagement features, such as fasteners, teeth, protrusions, grips, textured surfaces, etc. for engaging with the anatomy.

Figure 17B:
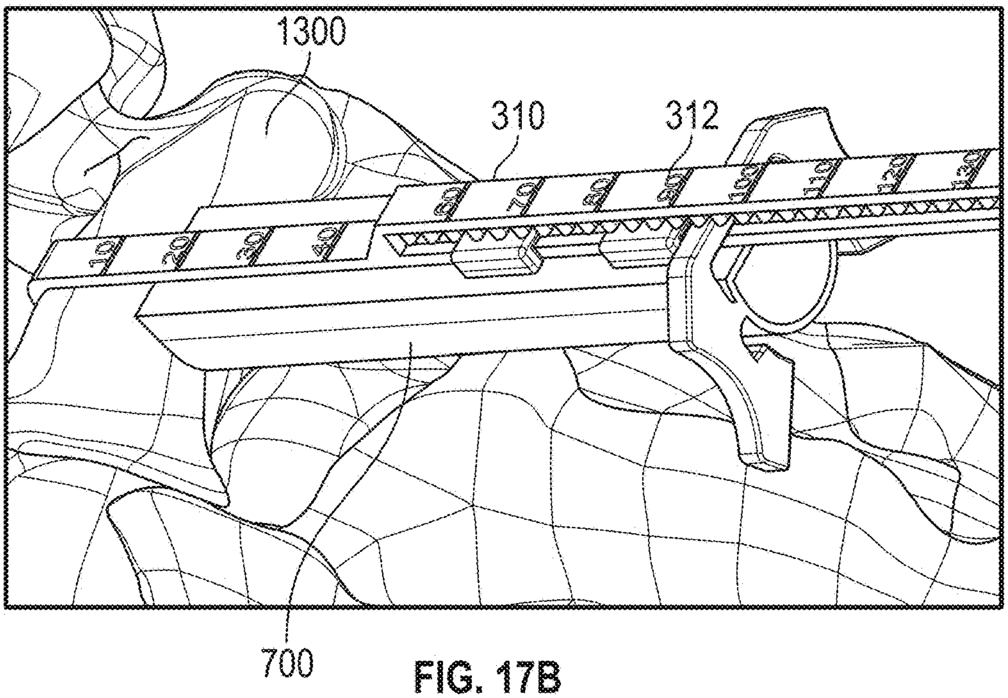
FIG. 17B depicts an example of the decompression system of FIG. 17A positioned adjacent to the target anatomy.

As shown in FIG. 17B, in certain embodiments in which the target area is a lamina, the hook 311 may be advanced over the superior side the lamina before engaging with the lamina.

Referring to FIG. 17B, when the working channel 700 is coupled to instrument shuttle 310 around the target anatomy 1300, the working channel 700 may be angled cephalad up the spine. Hook 311 can direct the working channel 700 to the desired angle by coupling onto the target anatomy 1300. Angling the working channel 700 up the spine can help prevent nerve or spinal damage. As previously described, placement of the working channel 700 can help protect surrounding bones and tissue. In some embodiments, the instrument shuttle 310 may have markings 312 on the length to indicate position of the working channel 700. In some embodiments, the markings 312 may provide a gauge to indicate a depth of an incision. In some embodiments, the markings 312 may provide a gauge to indicate how far the instrument shuttle 310 and/or working channel 700 have advanced into an incision. In some embodiments, different working channels 700 having different dimensions (diameter, length, etc.) can be provided for use within incisions of different sizes (e.g., depths). In some embodiments, the markings 312 can provide an indication of the depth of an incision, and a user may use this information to select a working channel 700 having an appropriate size (e.g., length). In some embodiments, the guard 300 may include markings 312 having any of the same or similar features and/or functions as the markings 312 of the instrument shuttle 310.

Figure 18A:
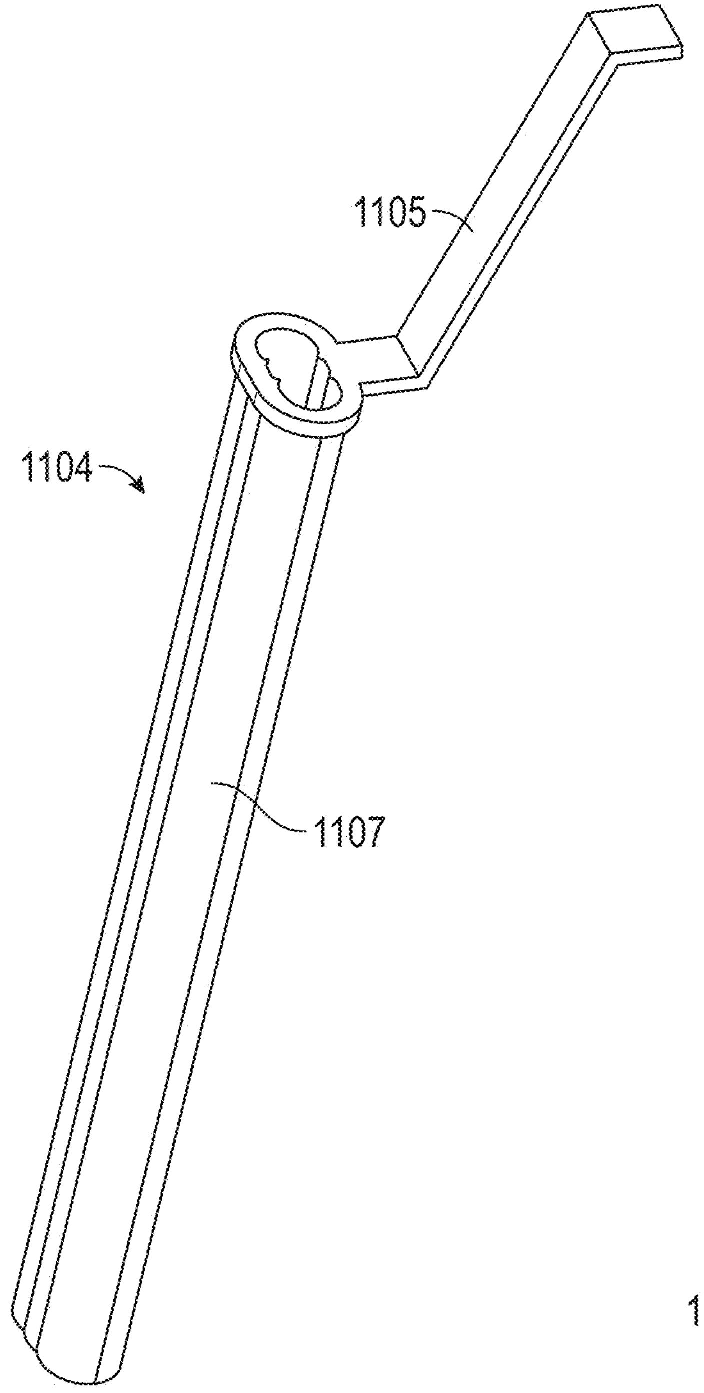
FIG. 18A depicts a perspective view of an embodiment of a guide.

FIG. 18A illustrates an embodiment of a channel divider or guide 1104. The guide 1104 can be used with the working channel 700 to provide one or more narrower channels for advancing instruments to the target area, as described further herein. In some embodiments, the guide 1104 can include a body 1107 defining one or more channels for advancing instruments to the target area.

Figure 18B:
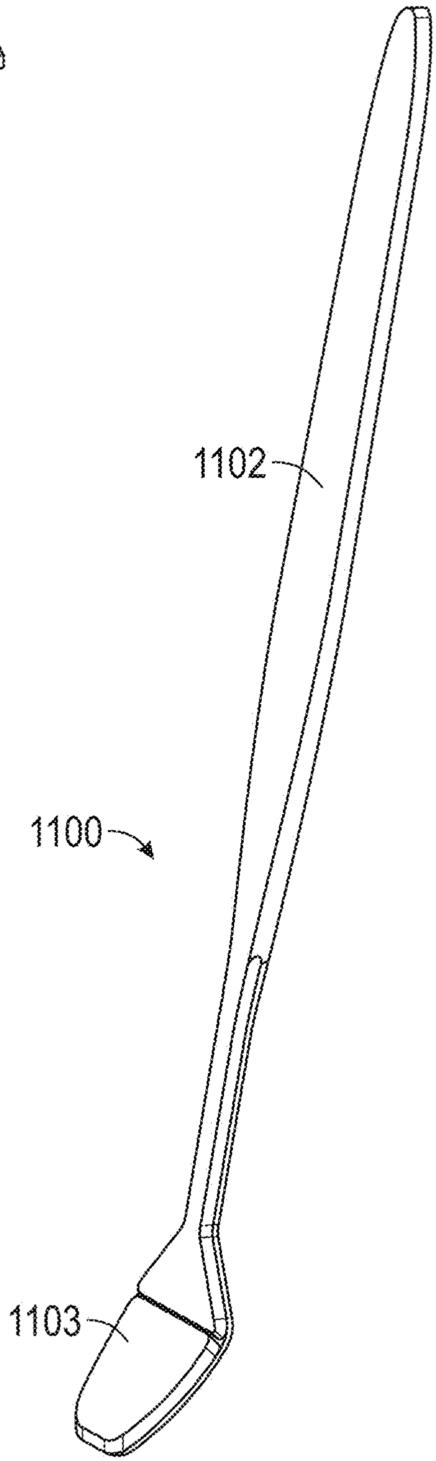
FIG. 18B depicts a perspective view of an embodiment of a guard.

FIG. 18B illustrates an embodiment of a guard 1100. The guard 1100 can include a guard plate 1103. The guard plate 1103 can include any of the same or similar features and/or functions as the guard plate 305 and vice versa. In contrast to certain embodiments of the guard 300, the guard 1100 is not part of an instrument shuttle for coupling to and advancing additional instruments, such as the working channel 700. Instead, in certain embodiments, the guard 1100 can be a separate instrument that can be advanced through the working channel 700. In some embodiments, when the target area is a lamina, a separate guard 1100 may be beneficial for traversing to the lamina when approaching the lamina along a path parallel or generally parallel to the lamina as shown, for example, in FIGS. 18C and 18D.

In some embodiments, the guard 1100 may have an elongated handle 1102. The elongated handle 1102 can be manipulated to maneuver the guard 1100 through muscle and other tissue.

At the distal end of the handle 1102, the guard plate 1103 may extend at a fixed angle form the handle. The fixed angle may be 15 degrees, 30 degrees, 45 degrees, 60 degrees, 75 degrees, 90 degrees, less than 15 degrees, between 0 degrees and 30 degrees, between 15 degrees and 30 degrees, between 30 degrees and 45 degrees, between 45 degrees and 60 degrees, between 60 degrees and 75 degrees, between 75 degrees and 90 degrees, between 15 degrees and 90 degrees, between 30 degrees and 60 degrees, between 60 degrees and 90 degrees, between 45 degrees and 90 degrees, or any other suitable angle. In other embodiments, the guard plate 1103 may extend generally parallel to the handle 1102. Shallow angles (e.g., parallel to the handle 1102, less than 15 degrees, or less than 30 degrees) may be beneficial when approaching parallel to or generally parallel to the lamina or target anatomy, which may be a precise and tight space. In certain embodiments, the guard plate 1103 may be pivotable (e.g., pivotably coupled to the handle 1102). In certain embodiments, the guard plate 1103 can be advanced below the inferior side of the lamina.

The guard 1100 and/or guard plate 1103 can be various shapes and sizes depending on the area needing to be protected. In some embodiments, the guard 1100 can help steady the working channel 700 acting as another point to engage with the target anatomy 1300.

Figure 18C:
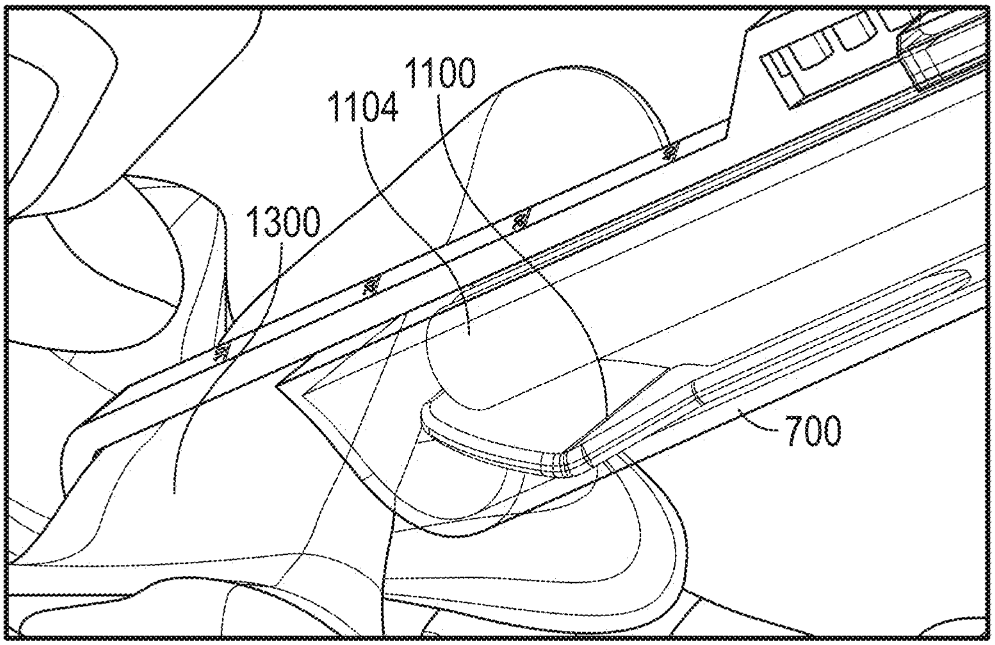
FIG. 18C depicts an example of the decompression system of FIG. 17A positioned adjacent to the target anatomy.
Figure 18D:
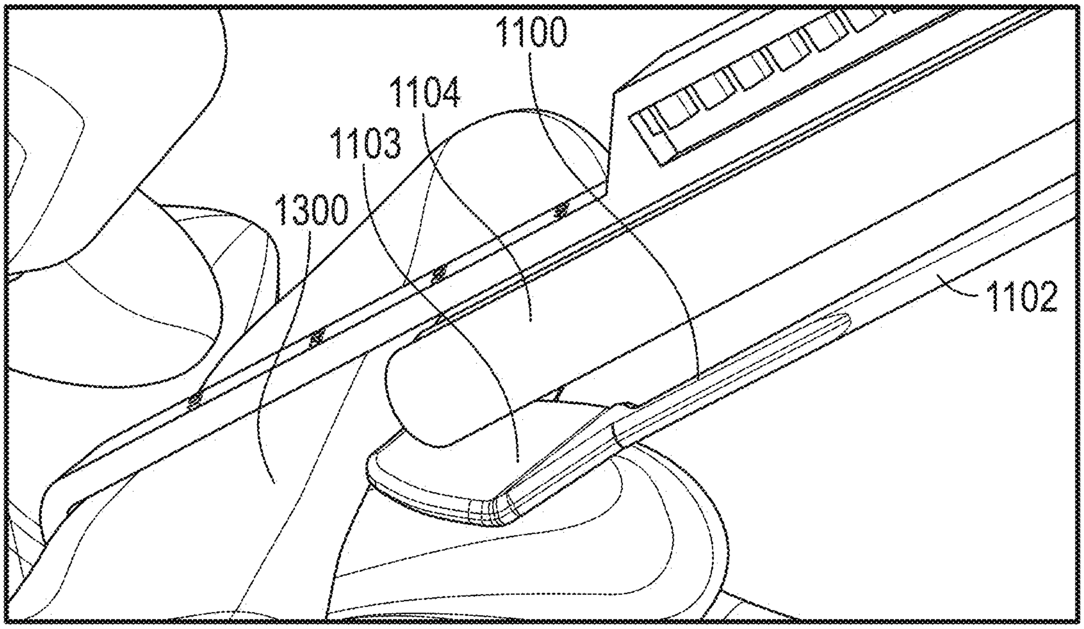
FIG. 18D depicts an example of the decompression system of FIG. 17A positioned adjacent to the target anatomy.

FIG. 18C illustrates the guide 1104 and guard 1100 within the working channel 700 adjacent the target anatomy 1300 with the working channel shown as transparent to show the interior of the working channel. FIG. 18D illustrates the guide 1104 and guard 1100 adjacent the target anatomy 1300 without showing the working channel 700. In some embodiments, once the working channel 700 is placed, the working channel 700 can be used to direct various instruments to the target anatomy 1300. For example, the guard 1100 can optionally be inserted into the working channel 700 and advanced to the target anatomy (e.g., to an underside of the target anatomy) to protect areas of the target anatomy 1300 or adjacent anatomical areas from unintentional damage, for example, as described with respect to the guard 300.

In some embodiments, the guide 1104 may be inserted into the working channel 700. The guide 1104 can be inserted into the working channel after the working channel 700 and hook 311 are positioned at the target anatomy. In some embodiments, the guide 1104 can be inserted into the working channel after the guard 1100 is positioned at the target anatomy. In other embodiments, the guard 1100 may be advanced down in the guide 1104. In some embodiments, the guard 1100 may be advanced outside of the guide 1104.

During a procedure, various tools may be delivered to the bone. The guide 1104 may be used to guide tools to a specific area of the target anatomy 1300. The guide 1104 may also protect surrounding tissue and bone from damage. In some embodiments, the guard 300 can be used to guide the guide 1104 through the working channel 700. In some embodiments, the guide 1104 may be used without the guard 1100.

Figure 19A:
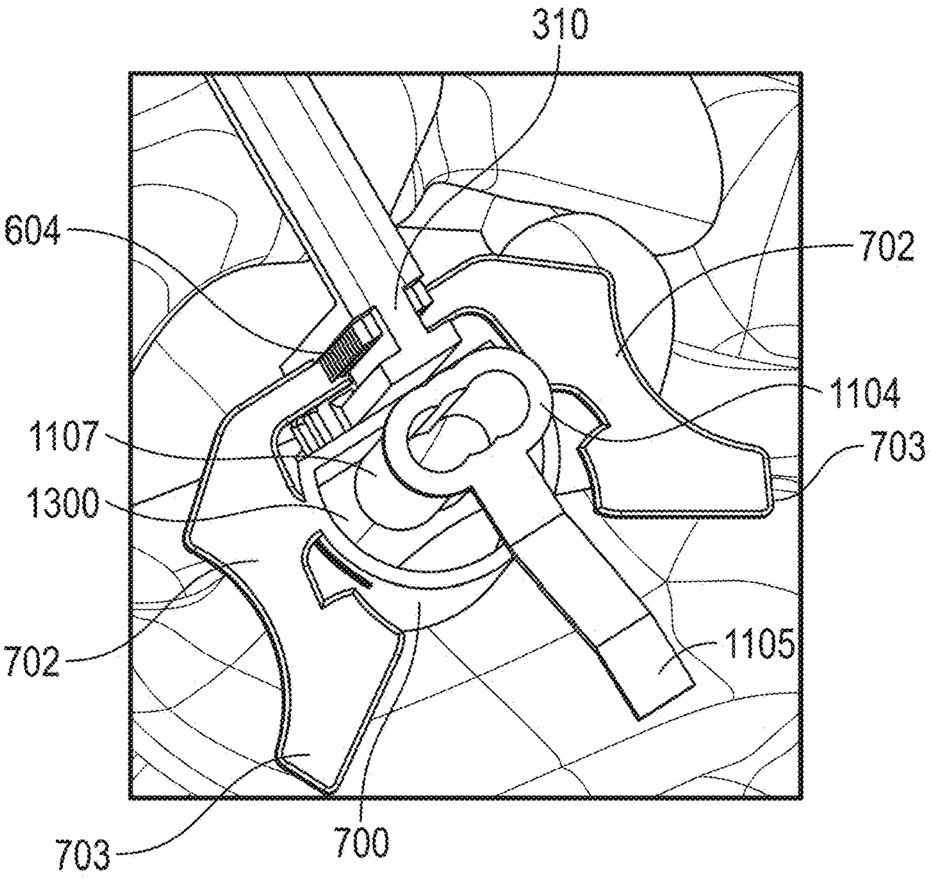
FIG. 19A depicts an example of the decompression system of FIG. 17A positioned adjacent to the target anatomy.
Figure 19B:
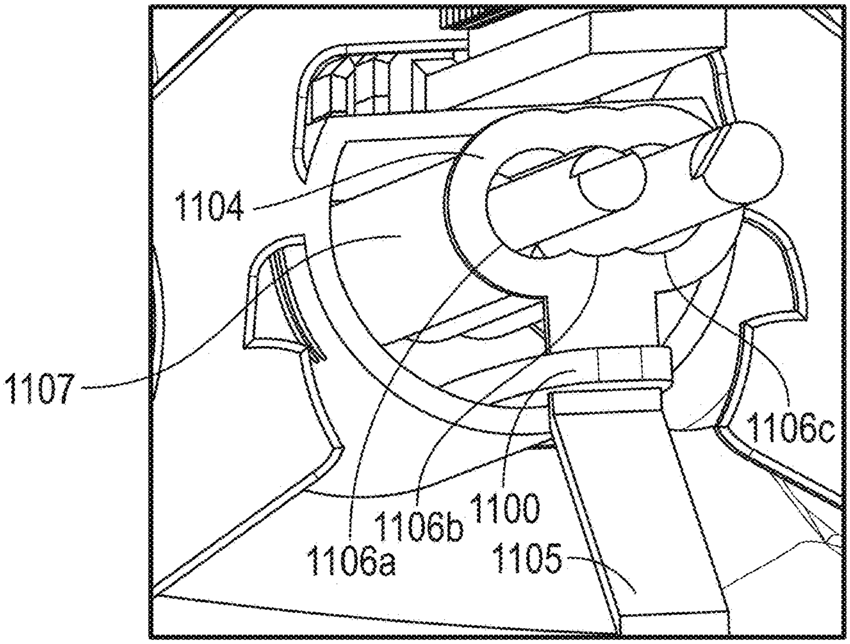
FIG. 19B depicts an example of the decompression system of FIG. 17A positioned adjacent to the target anatomy.

FIG. 19A illustrates a top view of the guide 1104 within the working channel 700 at the target anatomy 1300. The guide 1104 may have a handle 1105. The handle 1105 can prevent the guide 1104 from advancing too far into the working channel 700. The handle 1105 may also provide easier manipulation of the guide 1104 by the operator. In some embodiments, the handle 1105 of the guide 1104 may be used to couple to the guard 1100, as depicted in FIG. 19B. Coupling of components together can help keep the tools secured at the target anatomy 1300.

Referring to FIG. 19B, the guide 1104 is shown positioned within the working channel 700 with the guard 1100. In some embodiments, the guide 1104 may have one or more channels or barrels to accommodate various instruments and tools. In embodiments in which the guide 1104 includes multiple channels, the guide 1104 may also be referred to as a multi-channel or multi-barrel guide. In some embodiments, guide 1104 may have one, two, three, or more channels. Multiple channels may allow for a more precise trajectory of a tool advanced along one of the channels to different locations within the target anatomy 1300. In some embodiments, multiple channels may have different dimensions and/or shapes to accommodate different tools. In some embodiments, multiple channels may allow for the advancement of multiple tools simultaneously.

In some embodiments, the body 1107 of the guide 1104 may be shaped, sized, or otherwise configured to define three channels, 1106*a*, 1106*b*, and 1106*c*. In some embodiments, each of the channels 1106*a-c* in the guide 1104 may have a different shape and/or diameter to accommodate the shapes or dimensions of different tools. In some embodiments, the three channels may be all identically sized. The guide 1104 may be positioned within the working channel 700 such that channel 1106*a* is lined up with the target anatomy 1300. Similarly, channel 1106*b* or channel 1106*c* may be lined up with the target anatomy 1300.

FIG. 19B depicts the proximal ends of two instruments inserted into the guide 1104. As shown, a first instrument is positioned within the channel 1106*a* and a second instrument is positioned within the channel 1106*b*. While multiple instruments are shown within the guide 1104, in some embodiments, the guide 1104 may be used to advance a single instrument at one time via one of the channels 1106*a-c*. In some embodiments, the channels 1106*a-c* can allow a user to select a particular trajectory of a single instrument (e.g., by advancing the instrument down one of the channels). In some embodiments, a user may advance a single instrument down different channels 1106*a-c* at different times during a procedure. In some embodiments, a user may advance different instruments down different channels 1106*a-c* at different times during a procedure. In certain embodiments, use of a multi-channel guide 1104 may be beneficial in instances where the approach to the target anatomy requires a more precise trajectory, for example, if approaching the lamina along a path parallel or generally parallel to the lamina as shown, for example, in FIGS. 18C and 18D. In other embodiments, for example, when approaching perpendicular or generally perpendicular to the lamina as shown in FIG. 16, a working channel 700 may be used to advance instruments without using a guide 1104.

In some embodiments, multiple instruments can be positioned within two or more of the channels 1106*a-c* at the same time. In some embodiments, the channels 1106*a-c* can be used for advancement of multiple instruments simultaneously. Alternatively, a first instrument may be advanced through a first channel 1106*a-c* and a second instrument can be advanced through a second channel 1106*a-c* while the first instrument is still positioned in the first channel 1106*a*.

As described herein, the one or more instruments (e.g., a trephine, a drill, a kerrison, a burr, a reamer, etc.) can be advanced through the guide 1104 to drill or ream through the target anatomy (e.g., to create holes in the target anatomy). The instrument(s) may a create void and open up the canal. Once the holes are created, the instrument(s) may be removed from the guide 1104. In some embodiments, the guide 1104 may be a drill guide. In some embodiments, two or more of the channels 1106*a-c* can be used to create pilot holes to collectively make a larger opening in the target anatomy.

After the instrument(s) are removed from the guide 1104, the guide 1104 may be removed from the working channel 700. After removal of the guide 1104 from the working channel 700 the surgical site can be visualized down the working channel 700, for example, using a light source, loupes, a microscope, and/or the naked eye to determine if adequate decompression was performed. In some embodiments, a light source, loupes, and/or a microscope may be coupled to a portion of the decompression system 351, such as the lip 802 of the working channel 700. The light source, loupes, and/or microscope may be part of a decompression system, such as decompression system 350 or decompression system 351. In some embodiments, visualization of the surgical site can be performed with the guide 1104 still in place. In some embodiments, a pituitary or rongeur may be used to determine if more bone needs to be decompressed. In some embodiments, if it is determined that more decompression should be performed, additional drilling or reaming can be performed (e.g., through the working channel 700 and/or guide 1104).

In some embodiments, one or more instruments for performing a decompression procedure, such as a trephine, drill, kerrison, burr, reamer or other instrument to cut or alter the target anatomy, may be advanced through the working channel 700 to the target area 1300 without the guide 1104.

Although the guide 1104 is shown within the decompression system 351, in other embodiments, the guide 1104 may as be used within the decompression system 350. The guide 1104 can be inserted and used with a working channel 700 coupled to a guard 300 as described herein.

Figure 20A:
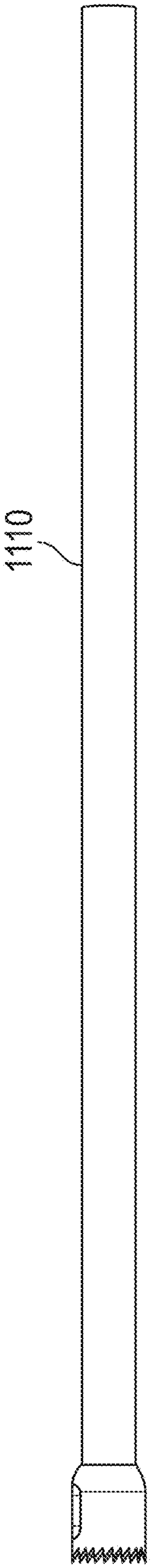
FIG. 20A depicts a side view of an embodiment of a trephine.
Figure 20B:
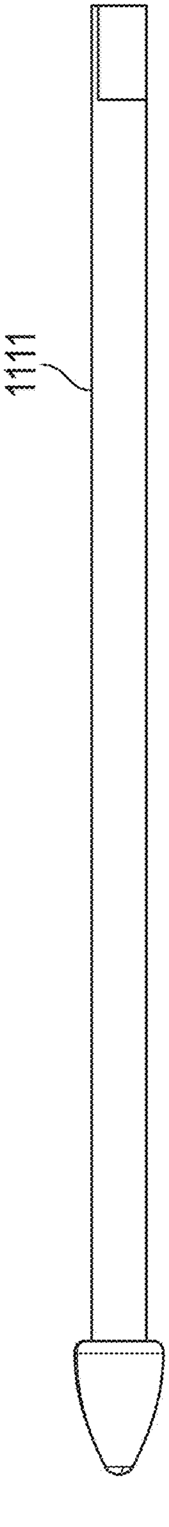
FIG. 20B depicts a side view of an embodiment of a drill burr.
Figure 20C:
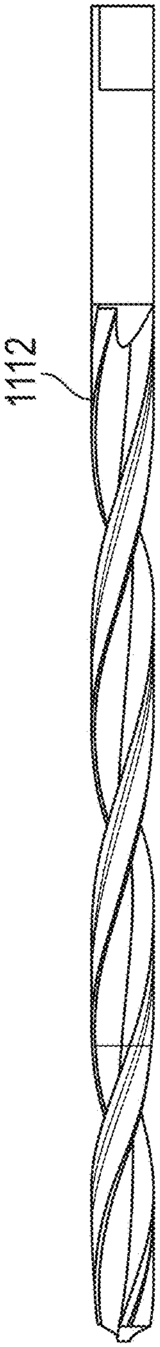
FIG. 20C depicts a side view of an embodiment of a drill bit.

FIGS. 20A-C depict embodiments of instruments that may be used with the guide 1104 and/or working channel 700, either separately or simultaneously. In some embodiments, the instruments may be part of a decompression system 350 or decompression system 351. FIG. 20A depicts a trephine 1110. FIG. 20B depicts an embodiment of a drill burr 1111. FIG. 20C depicts an embodiment of a drill bit 1112. The instruments may be used to create holes in the target anatomy. The instruments may be sharp or dull and/or serrated to depending on physician needs and/or risk to the patient. Any of the tools previously described herein may be used in conjunction with the guide 1104, working channel 700, and/or guard 1100 as described. In some embodiments, several tools may be used in sequence to remove portions of the bone. For example, the surgeon can use a kerrison, drill, trephine 1110, drill burr 1111, drill 1112, reamer or other instrument to remove all or part of the lamina and open the canal. A trephine 1000 such as the one described in FIG. 10 can be used in combination with the working channel 700 and/or guide 1104. Any of the prior medical instruments or tools previously described herein may be used in combination with the working channel 700 and/or guide 1104.

Any of the devices or systems described herein can be used with navigation, robotics, and/or augmented reality to visualize placement of the devices or systems, including the scalpel 106, the guard 300, instrument shuttle 310, the guard plate 305, the hook 311, the guide 1104, the trephine 1110, the drill burr 1111, the drill bit 1112, rongeurs, pituitarys, and/or any other instruments which contribute to decompression and/or the placement of any of the aforementioned instruments. For example, any of the instruments may attach to one or more navigation markers (e.g., spheres or navigation registers) to allow for visualization or other tracking of the position of the instruments in space relative to the patient to allow for precise placement and/or prevent injury. In some embodiments, the instrument(s) may attach to the navigation markers via clips either on the instruments or on the markers. In some embodiments, the instrument(s) may attach to a navigation guide having one or more navigation markers attached thereto.

In some embodiments, any of the working channel 700, guide 1104, or dilator tubes may be radiolucent. In some embodiments, a portion of any of the working channel 700, guide 1104, or dilator tubes (e.g., a distal end portion) may be radiolucent (e.g., to provide a target for navigation). In other embodiments, any of the working channel 700, guide 1104, or dilator tubes may be non-radiolucent e.g., to avoid obscuring other radiolucent materials in x-ray or fluoroscopy.

In some embodiments, one or more of the instruments described herein can be provided in a kit. A kit may include one or more of a scalpel guide 100, blade 201, a scalpel 106, a guide wire 200, a guard 300, a guard 1100, a working channel 700, a dilator, an instrument shuttle 310, a trephine 1000, a trephine 1110, a drill bur 1111, a drill bit 1112, a kerrison, a reamer, a pituitary, a rongeur, a light, a loupes, a microscope, a navigation marker, and a navigation guide. In some embodiments, a kit may include multiple of any of the foregoing, such as, for example, multiple guards. For example, a kit may include a guard 300 and a guard 1100 for approaching different anatomies. In some embodiments, a kit may include multiple guards 300 or multiple guards 1100 having guard plates with different fixed angles.

In certain embodiments, a decompression procedure can include one or more of the following steps. In some embodiments, an incision can be made, for example, using a scalpel such as scalpel 106. After the incision is made, one or more dilators may be advanced to a target area, such as a lamina. After dilation, a guard 300 can be advanced to the target area. After the guard 300 is advanced to the target area, a working channel 700 can be coupled to the guard 300 and advanced to the target area. The target area can be secured between a guard plate 305 of the guard 300 and a distal end 901 of the working channel 700. Then, one or more instruments can be advanced through the working channel to the target area and used to ream, drill, or otherwise cut away or remove bone to cause decompression.

In certain embodiments, a decompression procedure can include one or more of the following steps. In some embodiments, an incision can be made, for example, using a scalpel such as scalpel 106. After the incision is made, one or more dilators may be advanced to a target area, such as a lamina. After dilation, an instrument shuttle 310 can be advanced to the target area. The instrument shuttle 310 can engage the target area. After the instrument shuttle 310 engages the target area, a working channel 700 can be coupled to the instrument shuttle 310 and advanced to the target area. A guard 1100 can be advanced through or outside of the working channel 700. The target area can be secured between a guard plate 1103 of the guard 1100 and a distal end 901 of the working channel 700. Then, one or more instruments can be advanced through the working channel to the target area and used to ream, drill, or otherwise cut away or remove bone to cause decompression. Alternatively, after the target area is secured between the guard plate 1103 and the distal end 901 of the working channel 700, a guide 1104 can be inserted into the working channel 700. One or more instruments can be advanced down one or more channels of the guide 1104 to the target area and used to ream, drill, or otherwise cut away or remove bone to cause decompression.

The decompression systems and devices described herein can be used for an approach parallel to or perpendicular to a target anatomical area, such as a lamina. For example, FIG. 16 shows a perpendicular approach in which a longitudinal axis of the working channel 700 (and/or any instruments advanced therethrough) and/or guard body 304 can be perpendicular or generally perpendicular to a top surface of the lamina. FIGS. 17B, and 18C-18D show a parallel approach in which a longitudinal axis of the instrument shuttle 310, working channel 700 (and/or any instruments advanced therethrough), guide 1104 (and/or any instruments advanced therethrough), and/or guard handle 1102 can be parallel or generally parallel to a top surface of the lamina.

While decompression at a lamina is described herein in certain examples, one of skill in the art would understand that the devices, systems, and methods described herein can be used for other anatomical locations and/or other procedures. For example, the guards described herein may be used to provide a safety stop and/or otherwise protect anatomical areas adjacent to a treatment area at which instruments are passed through or used for cutting, removing, and/or otherwise manipulating tissue.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Various combinations and subcombinations of the various features described herein are possible.

What is claimed is:

1. A method for performing a decompression surgery, the method comprising:

advancing a working channel to a lamina through an incision such that a distal end of the working channel engages the lamina;

advancing a guide into the working channel, the guide comprising a lumen configured to align with the lamina;

advancing an instrument through the lumen along a first path defined by the lumen; and advancing the instrument through the lumen along a second path defined by the lumen, wherein the guide prevents the instrument from advancing along the first path while the instrument is positioned within the lumen along the second path.

2. The method of claim 1, wherein advancing the working channel to the lamina comprises advancing the working channel substantially parallel to the lamina.

3. The method of claim 1, wherein the second path is substantially parallel to the first path.

4. The method of claim 1, further comprising forming a hole in the lamina using the instrument.

5. The method of claim 4, wherein forming the hole in the lamina comprises cutting the lamina with the instrument after advancing along the first path and cutting the lamina with the instrument after advancing along the second path.

6. The method of claim 5, wherein forming the hole in the lamina further comprises cutting the lamina with the instrument after advancing along a third path.

7. The method of claim 1, wherein the instrument comprises at least one of a reamer, a trephine, a burr, or a drill.

8. The method of claim 1, wherein the lumen of the guide comprises three channels.

9. The method of claim 1, wherein the distal end of the working channel is sloped to nest the lamina.

10. The method of claim 1, further comprising coupling a light source with a proximal end of the working channel.

11. A method for performing a decompression surgery, the method comprising:

advancing an instrument through a lumen of a guide along a first path, the first path aligned with a first portion of a lamina, wherein the guide is positioned within a working channel, wherein a distal end of the working channel is engaged with the lamina; and advancing the instrument through the lumen along a second path defined by the lumen, the second path aligned with a second portion of the lamina, wherein the guide prevents the instrument from advancing along the first path while the instrument is positioned within the lumen along the second path.

12. The method of claim 11, wherein advancing the working channel to the lamina comprises advancing the working channel substantially parallel to the lamina.

13. The method of claim 11, wherein the second path is substantially parallel to the first path.

14. The method of claim 11, further comprising forming a hole in the lamina using the instrument.

15. The method of claim 14, wherein forming the hole in the lamina comprises cutting the lamina with the instrument after advancing along the first path and cutting the lamina with the instrument after advancing along the second path.

16. The method of claim 15, wherein forming the hole in the lamina further comprises cutting the lamina with the instrument after advancing along a third path.

17. The method of claim 11, wherein the instrument comprises at least one of a reamer, a trephine, a burr, or a drill.

18. The method of claim 11, wherein the lumen of the guide comprises three channels.

19. The method of claim 11, wherein a distal end of the working channel is sloped to nest the lamina.

20. The method of claim 11, further comprising coupling a light source with a proximal end of the working channel.

* * * * *